United States Patent [19]
Barnett et al.

[11] Patent Number: 6,022,958
[45] Date of Patent: *Feb. 8, 2000

[54] CDNAS CODING FOR MEMBERS OF THE CARCINOEMBRYONIC ANTIGEN FAMILY

[75] Inventors: Thomas R. Barnett, East Haven; James J. Elting, Madison; Michael E. Kamarck, Bethany, all of Conn.; Axel W. Kretschmer, Wulfrath, Germany

[73] Assignee: Bayer Corporation, Tarrytown, N.Y.

[*] Notice: This patent is subject to a terminal disclaimer.

[21] Appl. No.: 08/468,859

[22] Filed: Jun. 6, 1995

Related U.S. Application Data

[62] Division of application No. 08/027,974, Mar. 8, 1993, which is a division of application No. 07/760,031, Sep. 13, 1992, Pat. No. 5,231,009, which is a division of application No. 07/274,107, Nov. 21, 1988, Pat. No. 5,122,599, which is a continuation-in-part of application No. 07/207,678, Jun. 16, 1988, abandoned, which is a continuation-in-part of application No. 07/060,031, Jun. 19, 1987, abandoned, which is a continuation-in-part of application No. 07/016,683, Feb. 19, 1987, abandoned, which is a continuation-in-part of application No. 06/896,361, Aug. 13, 1986, abandoned.

[51] Int. Cl.$^7$ ............................ C07H 21/04; C12N 15/11; C12N 1/21; C12N 15/79
[52] U.S. Cl. .................... 536/23.1; 536/23.5; 536/24.31; 435/252.3; 435/320.1
[58] Field of Search .................................. 536/22.1, 23.1, 536/23.5, 24.31; 435/6, 252.3, 320.1; 935/12, 16, 22, 33

[56] References Cited

U.S. PATENT DOCUMENTS

| | | |
|---|---|---|
| 3,663,684 | 5/1972 | Orkin et al. . |
| 3,697,638 | 10/1972 | Hansen . |
| 3,852,415 | 12/1974 | Vandervoorde . |
| 3,867,363 | 2/1975 | Hansen . |
| 3,927,193 | 12/1975 | Hansen et al. . |
| 3,956,258 | 5/1976 | Hansen . |
| 4,086,217 | 4/1978 | Hansen . |
| 4,140,753 | 2/1979 | Edington et al. . |
| 4,145,336 | 3/1979 | Edington et al. . |
| 4,180,499 | 12/1979 | Hansen . |
| 4,228,236 | 10/1980 | Jakstys et al. . |
| 4,272,504 | 6/1981 | Kim et al. . |
| 4,299,815 | 11/1981 | Hansen et al. . |
| 4,349,528 | 9/1982 | Koprowski et al. . |
| 4,467,031 | 8/1984 | Gallati et al. . |
| 4,489,167 | 12/1984 | Ochi et al. . |
| 4,578,349 | 3/1986 | Schaffel . |

FOREIGN PATENT DOCUMENTS

| | | |
|---|---|---|
| 92223 | 4/1983 | European Pat. Off. . |
| 92225 | 10/1983 | European Pat. Off. . |
| 83303759 | 1/1984 | European Pat. Off. . |
| 102008 | 3/1984 | European Pat. Off. . |
| 97373 | 4/1984 | European Pat. Off. . |
| 113072 | 7/1984 | European Pat. Off. . |
| 8402983 | 8/1984 | WIPO . |

OTHER PUBLICATIONS

Beauchemin, et al., Mol. Cell Biol., vol. 7, No. 9, pp. 3221–3230, (1987).
Cabilly, et al., Proceedings of the National Academy of Sciences of the USA, vol. 81, (1984), pp. 3273–3277.
Engvall, et al., Proceedings of the National Academy of Sciences of the USA, vol. 75 1978, pp. 1670–1674, Isolation and characterization of the normal crossreacting antigen: Homology of its $NH_2$–terminal amino acid sequence with that of carcinoembryonic antigen.
Engvall, et al., Proceedings of the National Academy of Sciences of the USA, vol. 75, (1978), pp. 1170–1174.
Glassman, et al. (1978), Biochem. Biophys. Res. Com., vol. 85, pp. 209–216.
Gold and Freedman, J. Exp. Med., vol. 121, pp. 439–462, (1965).
Harlow, et al. Mol. and Cell Biol. (1985), vol. 5, No. 7, pp. 1601–1610, "Molecular Cloning and In Vitro Expression of a cDNA Clone for Human Cellular Tumor Antigen pg. 53".
Harlow, et al., Mol. and Cell Biol., vol.5, No. 7, pp. 1001–1010, (1985).
T. Higashide, et al. CA107 100h (1987), "Preparation of the CEA mRNA for CEA gene cloning".
T. Higashide, Chemical Abstracts,vol. 105, No. 7, Aug. 17th 1986, p. 162, abstract No. 55557d, Columbus, Ohio, US;"Studies on DNA methylation and gene expression. With special reference to the onocodevelopmental protein genes", & Sapporo Igaku Zasshi 1986, 55 (2), 79–91.
T. Higashide, Igaku NoArjumi, vol. 140, pp. 827–828, (1987).
M.E. Kamarck, et al., Proceedings of the National Academy of Sciences of the USA, vol. 84, No. 16, Aug. 1987, pp. 5350–5354; "Carcinoembryonic antigen family: Expression in a mouse L–cell transfectant and characterization of a partial cDNA in bacteriophage lambdagt 11".
Larhammer, et al., Proceedings of the National Academy of Sciences of the USA, vol. 82,, pp. 1475–1479, (1985).
T. Maniatis, Molecular Cloning, A Laboratory Manual, Cold Spring Harbor, 1982, pp. 387–388.

(List continued on next page.)

*Primary Examiner*—Toni R. Scheiner
*Assistant Examiner*—Nancy A. Johnson
*Attorney, Agent, or Firm*—Sprung Kramer Schaefer & Briscoe

[57] ABSTRACT

A nucleic acid comprising a base sequence which codes for a CEA family member peptide sequence or nucleic acids having a base sequence hybridizable therewith, replicable recombinant cloning vehicles having an insert comprising such nucleic acid, cells transfected, infected or injected with such cloning vehicles, polypeptides expressed by such cells, synthetic peptides derived from the coding sequence of CEA family member nucleic acids, antibody preparations specific for such polypeptides, immunoassays for detecting CEA family members using such antibody preparations and nucleic acid hybridization methods for detecting CEA family member nucleic acid sequences using a nucleic acid probe comprising the above described nucleic acid.

5 Claims, 1 Drawing Sheet

OTHER PUBLICATIONS

Neumaier, et al., J. Biol. Chem., vol. 263, pp. 3202–3207, (1988).

Oikawa, et al., Biochem. Biophys. Res. Comm., vol. 142, No. 2, pp. 511–518, (1978).

Oikawa, et al., Biochem. Biophys. Res. Comm., vol. 144, No. 2, pp. 634–642, (1987).

Oikawa, et al., Biochem. Biophys. Res. Comm., vol. 146, No. 2, pp. 464–469, (1987).

Paxton, et al. (1985), Abst. Int., Soc. Oncodev. Biol. Med., p. 47.

Rogers, et al. (1983), Biochim. Biophys. Acta vol. 695, pp. 227–249.

Sapporo Igaku Zasshi, vol. 55, No. 2, pp. 79–91 (1986), "Studies of DNA Methylation and Gene Expression".

J.E. Shively, et al., Chemical Abstracts, vol. 101, No. 21, 19th, Nov. 1984, p. 189, abstract No. 185160x, Columbus, Ohio, US; "Structural studies on carcinoembryonic antigen: molecular cloning o carcinoembryonic antigen using mixed synthetic oligonucleotide probes", & Prog. Cancer Res. Ther. 1984, 29 (Markers Colonic Cell Differ), 147–57.

Shively, et al., Prog. Cancer Res. Therapy, vol. 29, pp. 147–157, (1984).

Springer–Verlag, Practical Methods Mol. Biol., 1981 pp. 145–146.

Suggs, et al. (1981), Proceedings of the National Academy of Sciences of the USA, vol. 78, pp. 6613–6617.

Tawaragi, et al., Biochem. Biophys. Res. Comm., vol. 150, No. 1, pp. 89–96, (1988).

J.A. Thompson, et al., Proceedings of the National Academy of Sciences of the USA, vol. 84, No. 9, May 1987, pp. 2965–2969; "Molecular cloning of a gene belonging to the carcinoembryonic antigen gene family and discussion of a domain model".

Young, et al., Proceedings of the National Academy of Sciences of the USA, vol. 80, pp. 1194–1198, (1983).

W. Zimmermann, et al. Proceedings of the National Academy of Sciences of the USA, vol. 84, No. 9, May 1987, pp. 2960–2964; "Isolation and characterization of cDNA clones encoding the human carcinoembryonic antigen reveals a highly conserved repeating structure".

W. Zimmerman, et al., Chemical Abstracts, vol. 100, No. 23, Jun. 4th, 1984, p. 216, abstract No. 187487n, Columbus, Ohio, US; "Characterization of messenger RNA specific for carcinoembryonic antigen", & Ann. NY. Y. Acad. Sci. 1983, 417 (Oncodev. Biol. Med.), 21–30.

Zimmerman, et al., Annals. New York Academy of Sciences, pp. 21–30 (1983).

Paxton, et al.; Proceedings of National Academy of Sciences, vol. 84, pp. 920–924, (1987).

Barnett, Tumor Biology vol. 8 p. 339 Nov.–Dec. 1987.

Shively and Beatty CRC Critical Reviews in Oncology/Hematology 2:355–399, 1985.

TM1(CEA-(c))

TM2(CEA-(e))

TM3(CEA-(f))

TM4(CEA-(g))

CDNAS CODING FOR MEMBERS OF THE CARCINOEMBRYONIC ANTIGEN FAMILY

This application is a divisional of application Ser. No. 08/027,974, filed Mar. 8, 1993, now pending; which is a divisional of Ser. No. 07/760,031, filed Sep. 13, 1992 issued to U.S. Pat. No. 5,231,009; which is a division of Ser. No. 07/274,107, filed Nov. 21, 1988 issued to U.S. Pat. No. 5,122,599; which is a CIP of Ser. No. 07/207,678 filed Jun. 16, 1988, now abandoned; which is a CIP of Ser. No. 07/060,031 filed Jun. 19, 1987, now abandoned; which is a CIP of Ser. No. 07/016,683 filed Feb. 19, 1987, now abandoned; which is a CIP of Ser. No. 06/896,361 filed Aug. 13, 1986, now abandoned.

BACKGROUND OF THE INVENTION

1. Field of the Invention

The present invention concerns nucleic acid sequences which code for carcinoembryonic antigen (CEA) antigen family peptide sequences.

2. Background Information

Carcinoembryonic antigen was first described by Gold and Freedman, *J. Exp. Med.*, 121, 439–462, (1965). CEA is characterized as a glycoprotein of approximately 200,000 molecular weight with 50–60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do not return to normal often indicate incomplete resection of the tumor or the presence of additional tumor sites in the patient. After returning to normal levels, subsequent rapid rises in serum CEA levels usually indicate the presence of metastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such an inflammatory liver diseases and also in smokers. It is important that immunoassays used for the monitoring of cancer patient status not be interfered with by these other CEA-like antigens. Conversely, it is important to be able to distinguish the antigens by immunoassays because of the possibility that different tumor types may preferentially express different forms of CEA. If so, then the ability to reliably measure the different forms of CEA can provide the means to diagnose or more successfully treat different forms of cancer.

The members of the "CEA family" share some antigenic determinants. These common epitopes are not useful in distinguishing the members of the antigen family and antibodies recognizing them are of little use for measuring tumor-specific CEA levels.

U.S. Pat. No. 3,663,684, entitled "Carcinoembryonic Antigen and Diagnostic Method Using Radioactive Iodine", concerns purification and radioiodination of CEA for use in a RIA.

U.S. Pat. No. 3,697,638 describes that CEA is a mixture of antigens (components A and B in this case). U.S. Pat. No. 3,697,638 mentions methods for separating and radioiodinating each component and their use in specific RIA's.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labelling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-S1 and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65 to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen—After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen—Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or Tissue—for Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

DEFINITIONS

Nucleic Acid Abbreviations

| | |
|---|---|
| A | adenine |
| G | guanine |
| C | cytosine |
| T | thymidine |
| U | uracil |

DEFINITIONS

Amino Acid Abbreviations:

| | |
|---|---|
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG SEQ ID NO: 10 may be translated in three reading frames or phases, each of which affords a different amino acid sequence

| | | |
|---|---|---|
| GCT GGT TGT AAG | Ala–Gly–Cys–Lys | SEQ ID NO: 11 |
| G CTG GTT GTA AG | Leu–Val–Val | SEQ ID NO: 12 |
| GC TGG TTG TAA G | Trp–Leu–(STOP) | SEQ ID NO: 13. |

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

cDNA Expression Vector—A procaroytic cloning vehicle which also contains sequences of nucleotides that facilitate expression of cDNA sequences in eucaroytic cells. These nucleotides include sequences that function as eucaryotic promoter, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referred to herein concerns the microinjection (use of a small syringe) of DNA into a cell.

CEA antigen family (CEA gene family)—a set of genes (gene family) and their products (antigen family) that share nucleotide sequences homologous to partial cDNA LV-7 (CEA-(a)) and as a result of theses similarities also share a subset of their antigenic epitopes. Examples of the CEA antigen family include CEA (=CEA-(b)), transmembrane CEA (TMCEA)=CEA-(c) and normal crossreacting antigen NCA (=CEA-(d)).

SUMMARY OF THE INVENTION

The present invention concerns the following DNA sequences designated as TM-2 (CEA-(e)), TM-3 (CEA-(f)), TM-4 (CEA-(g)), KGCEA1 and KGCEA2, which code for CEA antigen family peptide sequences or nucleic acids having a base sequence (DNA or RNA) that are hybridizable therewith:

```
SEQUENCE AND TRANSLATION OF cDNA OF TM-2(SEQ ID NO:1)

10                  30                  50
               .                   .                   .
CAGCCGTGCTCGAAGCGTTCCTGGAGCCCAAGCTCTCCTCCACAGGTGAAGACAGGGCCA 70                  90                 110
               .                   .                   .
GCAGGAGACACCATGGGGCACCTCTCAGCCCCACTTCACAGAGTGCGTGTACCCTGGCAG
               MetGlyHisLeuSerAlaProLeuHisArgValArgValProTrpGln 130                 150                 170
               .                   .                   .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190                 210                 230
               .                   .                   .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250                 270                 290
               .                   .                   .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310                 330                 350
               .                   .                   .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370                 390                 410
               .                   .                   .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp
```

-continued

```
          430               450               470
           .                 .                 .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490               510               530
           .                 .                 .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550               570               590
           .                 .                 .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610               630               650
           .                 .                 .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670               690               710
           .                 .                 .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730               750               770
           .                 .                 .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790               810               830
           .                 .                 .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850               870               890
           .                 .                 .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910               930               950
           .                 .                 .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970               990              1010
           .                 .                 .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030              1050              1070
           .                 .                 .
ATAGTCACTGATAATGCTCTACCACAAGAAAATGGCCTCTCACCTGGGGCCATTGCTGGC
IleValThrAspAsnAlaLeuProGlnGluAsnGlyLeuSerProGlyAlaIleAlaGly 1090              1110              1130
           .                 .                 .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150              1170              1190
           .                 .                 .
CATTTCGGGAAGACCGGCAGGGCAAGCGACCAGCGTGATCTCACAGAGCACAAACCCTCA
HisPheGlyLysThrGlyArgAlaSerAspGlnArgAspLeuThrGluHisLysProSer 1210              1230              1250
           .                 .                 .
GTCTCCAACCACACTCAGGACCACTCCAATGACCCACCTAACAAGATGAATGAAGTTACT
ValSerAsnHisThrGlnAspHisSerAsnAspProProAsnLysMetAsnGluValThr 1270              1290              1310
           .                 .                 .
TATTCTACCCTGAACTTTGAAGCCCAGCAACCCACACAACCAACTTCAGCCTCCCCATCC
TyrSerThrLeuAsnPheGluAlaGlnGlnProThrGlnProThrSerAlaSerProSer 1330              1350              1370
           .                 .                 .
CTAACAGCCACAGAAATAATTTATTCAGAAGTAAAAAAGCAGTAATGAAACCTGTCCTGC
LeuThrAlaThrGluIleIleTyrSerGluValLysLysGln
```

-continued

```
          1390                1410                1430
            .                   .                   .
TCACTGCAGTGCTGATGTATTTCAAGTCTCTCACCCTCATCACTAGGAGATTCCTTTCCC 1450                1470                1490
            .                   .                   .
CTGTAGGGTAGAGGGGTGGGGACAGAAACAACTTTCTCCTACTCTTCCTTCCTAATAGGC 1510                1530                1550
            .                   .                   .
ATCTCCAGGCTGCCTGGTCACTGCCCCTCTCTCAGTGTCAATAGATGAAAGTACATTGGG 1570                1590                1610
            .                   .                   .
AGTCTGTAGGAAACCCAACCTTCTTGTCATTGAAATTTGGCAAAGCTGACTTTGGGAAAC 1630                1650                1670
            .                   .                   .
AGGGACCAGAACTTCCCCTCCCTTCCCCTTTTCCCAACCTGGACTTGTTTTAAACTTGCC 1690                1710                1730
            .                   .                   .
TGTTCAGAGCACTCATTCCTTCCCACCCCCAGTCCTGTCCTATCACTCTAATTCGGATTT 1750                1770                1790
            .                   .                   .
GCCATAGCCTTGAGGTTATGTCCTTTTCCATTAAGTACATGTGCCAGGAAACAGCGAGAG 1810                1830                1850
            .                   .                   .
AGAGAAAGTAAACGGCAGTAATGCTTCTCCTATTTCTCCAAAGCCTTGTGTGAACTAGCA 1870                1890                1910
            .                   .                   .
AAGAGAAGAAAATCAAATATATAACCAATAGTGAAATGCCACAGGTTTGTCCACTGTCAG 1930                1950                1970
            .                   .                   .
GGTTGTCTACCTGTAGGATCAGGGTCTAAGCACCTTGGTGCTTAGCTAGAATACCACCTA 1990                2010                2030
            .                   .                   .
ATCCTTCTGGCAAGCCTGTCTTCAGAGAACCCACTAGAAGCAACTAGGAAAAATCACTTG 2050                2070                2090
            .                   .                   .
CCAAAATCCAAGGCAATTCCTGATGGAAAATGCAAAAGCACATATATGTTTTAATATCTT 2110                2130                2150
            .                   .                   .
TATGGGCTCTGTTCAAGGCAGTGCTGAGAGGGAGGGGTTATAGCTTCAGGAGGGAACCAG 2170                2190                2210
            .                   .                   .
CTTCTGATAAACACAATCTGCTAGGAACTTGGGAAAGGAATCAGAGAGCTGCCCTTCAGC 2230                2250                2270
            .                   .                   .
GATTATTTAAATTGTTAAAGAATACACAATTTGGGGTATTGGGATTTTTCTCCTTTTCTC 2290                2310                2330
            .                   .                   .
TGAGACATTCCACCATTTTAATTTTTGTAACTGCTTATTTATGTGAAAAGGGTTATTTTT 2350                2370                2390
            .                   .                   .
ACTTAGCTTAGCTATGTCAGCCAATCCGATTGCCTTAGGTGAAAGAAACCACCGAAATCC 2410                2430                2450
            .                   .                   .
CTCAGGTCCCTTGGTCAGGAGCCTCTCAAGATTTTTTTTGTCAGAGGCTCCAAATAGAAA 2470                2490                2510
            .                   .                   .
ATAAGAAAAGGTTTTCTTCATTCATGGCTAGAGCTAGATTTAACTCAGTTTCTAGGCACC 2530                2550                2570
            .                   .                   .
TCAGACCAATCATCAACTACCATTCTATTCCATGTTTGCACCTGTGCATTTTCTGTTTGC
```

```
                        -continued
      2590              2610              2630
        .                 .                 .
CCCCATTCACTTTGTCAGGAAACCTTGGCCTCTGCTAAGGTGTATTTGGTCCTTGAGAAG 2650              2670              2690
        .                 .                 .
TGGGAGCACCCTACAGGGACACTATCACTCATGCTGGTGGCATTGTTTACAGCTAGAAAG 2710              2730              2750
        .                 .                 .
CTGCACTGGTGCTAATGCCCCTTGGGAAATGGGGCTGTGAGGAGGAGGATTATAACTTAG 2770              2790              2810
        .                 .                 .
GCCTAGCCTCTTTTAACAGCCTCTGAAATTTATCTTTTCTTCTATGGGGTCTATAAATGT 2830              2850              2870
        .                 .                 .
ATCTTATAATAAAAAGGAAGGACAGGAGGAAGACAGGCAAATGTACTTCTCACCCAGTCT 2890              2910              2930
        .                 .                 .
TCTACACAGATGGAATCTCTTTGGGGCTAAGAGAAAGGTTTTATTCTATATTGCTTACCT 2950              2970              2990
        .                 .                 .
GATCTCATGTTAGGCCTAAGAGGCTTTCTCCAGGAGGATTAGCTTGGAGTTCTCTATACT 3010              3030              3050
        .                 .                 .
CAGGTACCTCTTTCAGGGTTTTCTAACCCTGACACGGACTGTGCATACTTTCCCTCATCC 3070              3090              3110
        .                 .                 .
ATGCTGTGCTGTGTTATTTAATTTTTCCTGGCTAAGATCATGTCTGAATTATGTATGAAA 3130              3150              3170
        .                 .                 .
ATTATTCTATGTTTTTATAATAAAAATAATATATCAGACATCGAAAAAAAAAA SEQUENCE AND TRANSLATION OF cDNA OF TM-3(SEQ ID NO:2)
        10                30                50
         .                 .                 .
CAGCCGTGCTCGAAGCGTTCCTGGAGCCCAAGCTCTCCTCCACAGGTGAAGACAGGGCCA 70                90               110
         .                 .                 .
GCAGGAGACACCATGGGGCACCTCTCAGCCCCACTTCACAGAGTGCGTGTACCCTGGCAG
                MetGlyHisLeuSerAlaProLeuHisArgValArgValProTrpGln 130               150               170
         .                 .                 .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190               210               230
         .                 .                 .
ACTACTGAATCCATGCCATTCAATGTTGCAGAGGGGAAGGAGGTTCTTCTCCTTGTCCAC
ThrThrGluSerMetProPheAsnValAlaGluGlyLysGluBalLeuLeuLeuValHis 250               270               290
         .                 .                 .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310               330               350
         .                 .                 .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370               390               410
         .                 .                 .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp
```

-continued

```
          430              450              470
           .                .                .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490              510              530
           .                .                .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550              570              590
           .                .                .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610              630              650
           .                .                .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670              690              710
           .                .                .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730              750              770
           .                .                .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790              810              830
           .                .                .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850              870              890
           .                .                .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910              930              950
           .                .                .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970              990             1010
           .                .                .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030             1050             1070
           .                .                .
ATAGTCACTGAGCTAAGTCCAGTAGTAGCAAAGCCCCAAATCAAAGCCAGCAAGACCACA
IleValThrGluLeuSerProValValAlaLysProGlnIleLysAlaSerLysThrThr 1090             1110             1130
           .                .                .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer 1150             1170             1190
           .                .                .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1210             1230             1250
           .                .                .
GGCAACACCACCCTCAGCATAAACCCTGTCAAGAGGGAGGATGCTGGGACGTATTGGTGT
GlyAsnThrThrLeuSerIleAsnProValLysArgGluAspAlaGlyThrTyrTrpCys 1270             1290             1310
           .                .                .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1330             1350             1370
           .                .                .
AATGCTCTACCACAAGAAAATGGCCTCTCACCTGGGGCCATTGCTGGCATTGTGATTGGA
AsnAlaLeuProGlnGluAsnGlyLeuSerProGlyAlaIleAlaGlyIleValIleGly
```

-continued

```
              1390                  1410                  1430
               .                     .                     .
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450                  1470                  1490
               .                     .                     .
ACCGGCAGCTCAGGACCACTCCAATGACCCACCTAACAAGATGAATGAAGTTACTTATTC
ThrGlySerSerGlyProLeuGln 1510                  1530                  1550
               .                     .                     .
TACCCTGAACTTTGAAGCCCAGCAACCCACACAACCAACTTCAGCCTCCCCATCCCTAAC 1570                  1590                  1610
               .                     .                     .
AGCCACAGAAATAATTTATTCAGAAGTAAAAAAGCAGTAATGAAACCTGAAAAAAAAAA

1630
               .
AAAAAAAAAA
```

SEQUENCE AND TRANSLATION OF cDNA OF TM-4(SEQ ID NO:3)

```
              10                   30                    50
               .                    .                     .
CAGCCGTGCTCGAAGCGTTCCTGGAGCCCAAGCTCTCCTCCACAGGTGAAGACAGGGCCA 70                   90                    110
               .                    .                     .
GCAGGAGACACCATGGGGCACCTCTCAGCCCCACTTCACAGAGTGCGTGTACCCTGGCAG
           MetGlyHisLeuSerAlaProLeuHisArgValArgValProTrpGln 130                  150                   170
               .                    .                     .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190                  210                   230
               .                    .                     .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250                  270                   290
               .                    .                     .
AATCTGCCCCAGCAACTTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310                  330                   350
               .                    .                     .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370                  390                   410
               .                    .                     .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430                  450                   470
               .                    .                     .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490                  510                   530
               .                    .                     .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550                  570                   590
               .                    .                     .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610                  630                   650
               .                    .                     .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly
```

-continued

```
         670                 690                 710
          .                   .                   .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730                 750                 770
          .                   .                   .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790                 810                 830
          .                   .                   .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850                 870                 890
          .                   .                   .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910                 930                 950
          .                   .                   .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970                 990                1010
          .                   .                   .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030                1050                1070
          .                   .                   .
ATAGTCACTGATAATGCTCTACCACAAGAAAATGGCCTCTCACCTGGGGCCATTGCTGGC
IleValThrAspAsnAlaLeuProGlnGluAsnGlyLeuSerProGlyAlaIleAlaGly 1090                1110                1130
          .                   .                   .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150                1170                1190
          .                   .                   .
CATTTCGGGAAGACCGGCAGCTCAGGACCACTCCAATGACCCACCTAACAAGATGAATGA
HisPheGlyLysThrGlySerSerGlyProLeuGln 1210                1230                1250
          .                   .                   .
AGTTACTTATTCTACCCTGAACTTTGAAGCCCAGCAACCCACACAACCAACTTCAGCCTC 1270                1290                1310
          .                   .                   .
CCCATCCCTAACAGCCACAGAAATAATTTATTCAGAAGTAAAAAAGCAGTAATGAAACCT

1330
          .
GAAAAAAAAAAAAAAAAAA
```

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a CEA, as well as labelled forms of the polypeptide. The invention also relates to polypeptides having an amino acid sequence, i.e., synthetic peptides, or the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amino acids of the aforesaid expression product.

The invention further relates to an antibody preparation specific for the above described polypeptide.

Another aspect of the invention concerns an immunoassay method for detecting CEA or a functional equivalent thereof in a test sample comprising
 (a) contacting the sample with the above described antibody preparation, and
 (b) determining binding thereof to CEA in the sample.

The invention also is directed to a nucleic acid hybridization method for detecting a CEA or a related nucleic acid (DNA or RNA) sample in a test sample comprising
 (a) contacting the test sample with a nucleic acid probe comprising a nucleic acid, which comprises a base sequence which codes for a CEA peptide sequence or a base sequence that is hybridizable therewith, and (b) determining the formation of the resultant hybridized probe.

The present invention also concerns a method for detecting the presence of carcinoembryonic antigen or a functional equivalent thereof in an animal or human patient in vivo comprising a) introducing into said patient a labeled (e.g., a radio-opaque material that can be detected by X-rays, radio-labeled or labeled with paramagnetic materials that can be detected by NMR) antibody preparation according to the present invention and b) detecting the presence of such antibody preparation in the patient by detecting the label.

In another aspect, the present invention relates to the use of an antibody preparation according to the present invention for therapeutic purposes, namely, attaching to an antibody preparation radionuclides, toxins or other biological effectors to form a complex and introducing an effective amount of such complex into an animal or human patient, e.g., by injection or orally. The antibody complex would attach to CEA in a patient and the radionuclide, toxin or other biological effector would serve to destroy the CEA expressing cell.

DETAILED DESCRIPTION OF THE INVENTION

Figure 1A:
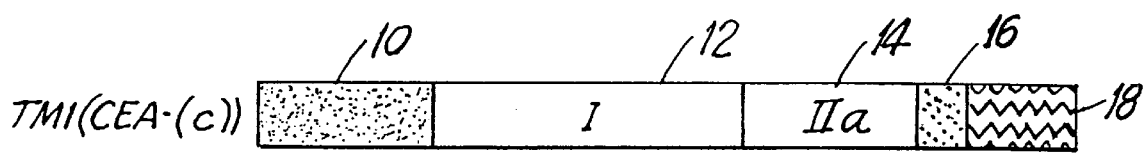
FIG. 1 is a schematic representation of the transmembrane CEA's

In parent applications, applicants described the following CEA's:

|         |                        | ATCC No. |
|---------|------------------------|----------|
| CEA-(a) | partial CEA (pcLV7)    |          |
| CEA-(b) | full coding CEA (pc 15LV7) | 67709 |
| CEA-(c) | TM-1 (FL-CEA; pc 19—22) | 67710 |
| CEA-(d) | NCA (pcBT 20)          | 67711    |

In the present application, applicants described the following CEA's:

|         |              | ATTC No. |
|---------|--------------|----------|
| CEA-(e) | TM-2 (pc E22)| 67712    |
| CEA-(f) | TM-3 (pc HT-6)| 67708   |
| CEA-(g) | TM-4.        |          |

ATCC Nos. 67708, 67709, 67710, 67711 and 67712 were all deposited with the American Type Culture Collection on May 25, 1988.

The sequences for CEA-(a), CEA-(b), CEA-(c) and CEA-(d) are given hereinbelow:

CEA-(a)(SEQ ID NO:4):

GG GGT TTA CAC AAC CAC CAC CCC ATC AAA CCC TTC ATC ACC AGC AAC AAC TCC AAC CCC GTG

GAG GAT GAG GAT GCT GTA GCC TTA ACC TGT GAA CCT GAG ATT CAG AAC ACA ACC TAC CTG

TGG TGG GTA AAT AAT CAG AGC CTC CCG GTC AGT CCC AGG CTG CAG CTG TCC AAT GAC AAC

AGG ACC CTC ACT CTA CTC AGT GTC ACA AGG AAT GAT GTA GGA CCC TAT GAG TGT GGA ATC

CAG AAC GAA TTA AGT GTT GAC CAC AGC GAC CCA GTC ACC CAG GCA TTC CTC TAT GGC CCA

GAC GAC CCC ACC ATT TCC CCC TCA TAC ACC TAT TAC CGT CCA GGG GTG GAA CCT CAG CCT

CTC TGC CAT GCA GCC TCT AAC CCA CCT GCA CAG TAT TCT TGG CTG ATT GAT GGG ACC GTC

CAG CAA CAC ACA CAA GAG CTC TTT ATC TCC AAC ATC ACT GAG AAG AAC AGC GGA CTC TAT

ACC TGC CAG GCC AAT AAC TCA GCC AGT GGC ACA GCA GGA CTA CAG TCA AGA CAA TCA CAG

TCT CTG CGG ATG CCC AAG CCC TCC ATC TCC AGC AAC AAC TCC AAA CCC GTG GAG GAC AAG

GAT CGC TGT GGC CTT CAC TGT GAA CCT GAG GCT CAG AAC ACA ACC TAC CTG TGG TGG GTA

AAT GGT CAG AGC CTC CCA GTC AGT CCC AGG CTG CAG CTG TCC AAT GGC AAC AGG ACC CTC

ACT CTA TTC AAT GTC ACA AGA AAT GAC GCA AGA GCC TAT GTA TGT GGA ATC CAG AAC TCA

GTG AGT GCA AAC CGC AGT GAC CCA GTC ACC CTG GAT GTC CTC TAT GGG CCG GAC ACC CCC

ATC ATT TCC CCC CC

CEA-(b)(SEQ ID NO:5):

```
              10                  30                  50
               .                   .                   .
CACCATGGAGTCTCCCTCGGCCCCTCCCCACAGATGGTGCATCCCCTGGCAGAGGCTCCTG
MetGluSerProSerAlaProProHisArgTrpCysIleProTrpGlnArgLeuLeu
```

```
              70                  90                 110
               .                   .                   .
CTCACAGCCTCACTTCTAACCTTCTGGAACCCGCCCACCACTGCCAAGCTCACTATTGAA
LeuThrAlaSerLeuLeuThrPheTrpAsnProProThrThrAlaLysLeuThrIleGlu 130                 150                 170
               .                   .                   .
TCCACGCCGTTCAATGTCGCAGAGGGGAAGGAGGTGCTTCTACTTGTCCACAATCTGCCC
SerThrProPheAsnValAlaGluGlyLysGluValLeuLeuLeuValHisAsnLeuPro 190                 210                 230
               .                   .                   .
CAGCATCTTTTTGGCTACAGCTGGTACAAAGGTGAAAGAGTGGATGGCAACCGTCAAATT
GlnHisLeuPheGlyTyrSerTrpTyrLysGlyGluArgValAspGlyAsnArgGlnIle 250                 270                 290
               .                   .                   .
ATAGGATATGTAATAGGAACTCAACAAGCTACCCCAGGGCCCGCATACAGTGGTCGAGAG
IleGlyTyrValIleGlyThrGlnGlnAlaThrProGlyProAlaTyrSerGlyArgGlu 310                 330                 350
               .                   .                   .
ATAATATACCCCAATGCATCCCTGCTGATCCAGAACATCATCCAGAATGACACAGGATTC
IleIleTyrProAsnAlaSerLeuLeuIleGlnAsnIleIleGlnAsnAspThrGlyPhe 370                 390                 410
               .                   .                   .
TACACCCTACACGTCATAAAGTCAGATCTTGTGAATGAAGAAGCAACTGGCCAGTTCCGG
TyrThrLeuHisValIleLysSerAspLeuValAsnGluGluAlaThrGlyGlnPheArg 430                 450                 470
               .                   .                   .
GTATACCCGGAGCTGCCCAAGCCCTCCATCTCCAGCAACAACTCCAAACCCGTGGAGGAC
ValTyrProGluLeuProLysproSerIleSerSerAsnAsnSerLysProValGluAsp 490                 510                 530
               .                   .                   .
AAGGATGCTGTGGCCTTCACCTGTGAACCTGAGACTCAGGACGCAACCTACCTGTGGTGG
LysAspAlaValAlaPheThrCysGluProGluThrGlnAspAlaThrTyrLeuTrpTrp 550                 570                 590
               .                   .                   .
GTAAACAATCAGAGCCTCCCGGTCAGTCCCAGGCTGCAGCTGTCCAATGGCAACAGGACC
ValAsnAsnGlnSerLeuProValSerProArgLeuGlnLeuSerAsnGlyAsnArgThr 610                 630                 650
               .                   .                   .
CTCACTCTATTCAATGTCACAAGAAATGACACAGCAAGCTACAAATGTGAAACCCAGAAC
LeuThrLeuPheAsnValThrArgAsnAspThrAlaSerTyrLysCysGluThrGlnAsn 670                 690                 710
               .                   .                   .
CCAGTGAGTGCCAGGCGCAGTGATTCAGTCATCCTGAATGTCCTCTATGGCCCGGATGCC
ProValSerAlaArgArgSerAspSerValIleLeuAsnValLeuTyrGlyProAspAla 730                 750                 770
               .                   .                   .
CCCACCATTTCCCCTCTAAACACATCTTACAGATCAGGGGAAAATCTGAACCTCTCCTGC
ProThrIleSerProLeuAsnThrSerTyrArgSerGlyGluAsnLeuAsnLeuSerCys 790                 810                 830
               .                   .                   .
CACGCAGCCTCTAACCCACCTGCACAGTACTCTTGGTTTGTCAATGGGACTTTCCAGCAA
HisAlaAlaSerAsnProProAlaGlnTyrSerTrpPheValAsnGlyThrPheGlnGln 850                 870                 890
               .                   .                   .
TCCACCCAAGAGCTCTTTATCCCCAACATCACTGTGAATAATAGTGGATCCTATACGTGC
SerThrGlnGluLeuPheIleProAsnIleThrValAsnAsnSerGlySerTyrThrCys 910                 930                 950
               .                   .                   .
CAAGCCCATAACTCAGACACTGGCCTCAATAGGACCACAGTCACGACGATCACAGTCTAT
GlnAlaHisAsnSerAspThrGlyLeuAsnArgThrThrValThrThrIleThrValTyr 970                 990                1010
               .                   .                   .
GCAGAGCCACCCAAACCCTTCATCACCAGCAACAACTCCAACCCCGTGGAGGATGAGGAT
AlaGluProProLysProPheIleThrSerAsnAsnSerAsnProValGluAspGluAsp
```

```
              1030          1050          1070
                .             .             .
GCTGTAGCCTTAACCTGTGAACCTGAGATTCAGAACACAACCTACCTGTGGTGGGTAAAT
AlaValAlaLeuThrCysGluProGluIleGlnAsnThrThrTyrLeuTrpTrpValAsn 1090          1110          1130
                .             .             .
AATCAGAGCCTCCCGGTCAGTCCCAGGCTGCAGCTGTCCAATGACAACAGGACCCTCACT
AsnGlnSerLeuProValSerProArgLeuGlnLeuSerAsnAspAsnArgThrLeuThr 1150          1170          1190
                .             .             .
CTACTCAGTGTCACAAGGAATGATGTAGGACCCTATGAGTGTGGAATCCAGAACGAATTA
LeuLeuSerValThrArgAsnAspValGlyProTyrGluCysGlyIleGlnAsnGluLeu 1210          1230          1250
                .             .             .
AGTGTTGACCACAGCGACCCAGTCATCCTGAATGTCCTCTATGGCCCAGACGACCCCACC
SerValAspHisSerAspProValIleLeuAsnValLeuTyrGlyProAspAsnProThr 1270          1290          1310
                .             .             .
ATTTCCCCCTCATACACCTATTACCGTCCAGGGGTGAACCTCAGCCTCTCCTGCCATGCA
IleSerProSerTyrThrTyrTyrArgProGlyValAsnLeuSerLeuSerCysHisAla 1330          1350          1370
                .             .             .
GCCTCTAACCCACCTGCACAGTATTCTTGGCTGATTGATGGGAACATCCAGCAACACACA
AlaSerAsnProProAlaGlnTyrSerTrpLeuIleAspGlyAsnIleGlnGlnHisThr 1390          1410          1430
                .             .             .
CAAGAGCTCTTTATCTCCAACATCACTGAGAAGAACAGCGGACTCTATACCTGCCAGGCC
GlnGluLeuPheIleSerAsnIleThrGluLysAsnSerGlyLeuTyrThrCysGlnAla 1450          1470          1490
                .             .             .
AATAACTCAGCCAGTGGCCACAGCAGGACTACAGTCAAGACAATCACAGTCTCTGCGGAG
AsnAsnSerAlaSerGlyHisSerArgThrThrValLysThrIleThrValSerAlaGlu 1510          1530          1550
                .             .             .
CTGCCCAAGCCCTCCATCTCCAGCAACAACTCCAAACCCGTGGAGGACAAGGATGCTGTG
LeuProLysProSerIleSerSerAsnAsnSerLysProValGluAspLysAspAlaVal 1570          1590          1610
                .             .             .
GCCTTCACCTGTGAACCTGAGGCTCAGAACACAACCTACCTGTGGTGGGTAAATGGTCAG
AlaPheThrCysGluProGluAlaGlnAsnThrThrTyrLeuTrpTrpValAsnGlyGln 1630          1650          1670
                .             .             .
AGCCTCCCAGTCAGTCCCAGGCTGCAGCTGTCCAATGGCAACAGGACCCTCACTCTATTC
SerLeuProValSerProArgLeuGlnLeuSerAsnGlyAsnArgThrLeuThrLeuPhe 1690          1710          1730
                .             .             .
AATGTCACAAGAAATGACGCAAGAGCCTATGTATGTGGAATCCAGAACTCAGTGAGTGCA
AsnValThrArgAsnAspAlaArgAlaTyrValCysGlyIleGlnAsnSerValSerAla 1750          1770          1790
                .             .             .
AACCGCAGTGACCCAGTCACCCTGGATGTCCTCTATGGGCCGGACACCCCCATCATTTCC
AsnArgSerAspProValThrLeuAspValLeuTyrGlyProAspThrProIleIleSer 1810          1830          1850
                .             .             .
CCCCCAGACTCGTCTTACCTTTCGGGAGCGAACCTCAACCTCTCCTGCCACTCGGCCTCT
ProProAspSerSerTyrLeuSerGlyAlaAsnLeuAsnLeuSerCysHisSerAlaSer 1870          1890          1910
                .             .             .
AACCCATCCCCGCAGTATTCTTGGCGTATCAATGGGATACCGCAGCAACACACACAAGTT
AsnProSerProGlnTyrSerTrpArgIleAsnGlyIleProGlnGlnHisThrGlnVal 1930          1950          1970
                .             .             .
CTCTTTATCGCCAAAATCACGCCAAATAATAACGGGACCTATGCCTGTTTTGTCTCTAAC
LeuPheIleAlaLysIleThrProAsnAsnAsnGlyThrTyrAlaCysPheValSerAsn
```

-continued

```
          1990                2010                2030
            .         .         .         .         .         .
TTGGCTACTGGCCGCAATAATTCCATAGTCAAGAGCATCACAGTCTCTGCATCTGGAACT
LeuAlaThrGlyArgAsnAsnSerIleValLysSerIleThrValSerAlaSerGlyThr 2050                2070                2090
            .         .         .         .         .         .
TCTCCTGGTCTCTCAGCTGGGGCCACTGTCGGCATCATGATTGGAGTGCTGGTTGGGGTT
SerProGlyLeuSerAlaGlyAlaThrValGlyIleMetIleGlyValLeuValGlyVal 2110                2130                2150
            .         .         .         .         .         .
GCTCTGATATAGCAGCCCTGGTGTAGTTTCTTCATTTCAGGAAGACTGACAGTTGTTTTG
AlaLeuIleEnd 2170                2190                2210
            .         .         .         .         .         .
CTTCTTCCTTAAAGCATTTGCAACAGCTACAGTCTAAAATTGCTTCTTTACCAAGGATAT 2230                2250                2270
            .         .         .         .         .         .
TTACAGAAAAGACTCTGACCAGAGATCGAGACCATCCTAGCCAACATCGTGAAACCCCAT 2290                2310                2330
            .         .         .         .         .         .
CTCTACTAAAAATACAAAAATGAGCTGGGCTTGGTGGCGCGCACCTGTAGTCCCAGTTAC 2350                2370                2390
            .         .         .         .         .         .
TCGGGAGGCTGAGGCAGGAGAATCGCTTGAACCCGGGAGGTGGAGATTGCAGTGAGCCCA 2410                2430                2450
            .         .         .         .         .         .
GATCGCACCACTGCACTCCAGTCTGGCAACAGAGCAAGACTCCATCTCAAA 2460       2470       2480       2490       2500
            *         *         *         *         *
 AAG AAA AGA AAA GAA GAC TCT GAC CTG TAC TCT TGA ATA CAA GTT TCT GAT ACC ACT 2510       2520       2530       2540       2550       2560
  *         *         *         *         *         *
 GCA CTG TCT GAG AAT TTC CAA AAC TTT AAT GAA CTA ACT GAC AGC TTC ATG AAA CTG 2570       2580       2590       2600       2610       2620
     *         *         *         *         *         *
 TCC ACC AAG ATC AAG CAG AGA AAA TAA TTA ATT TCA TGG GGA CTA AAT GAA CTA ATG 2630       2640       2650       2660       2670       2680
         *         *         *         *         *         *
 AGG ATA ATA TTT TCA TAA TTT TTT ATT TGA AAT TTT GCT GAT TCT TTA AAT GTC TTG 2690       2700       2710       2720       2730
           *         *         *         *         *
 TTT CCC AGA TTT CAG GAA ACT TTT TTT CTT TTA AGC TAT CCA CTC TTA CAG CAA TTT 2740       2750       2760       2770       2780       2790
  *         *         *         *         *         *
 GAT AAA ATA TAG TTT TGT GAA CAA AAA TTG AGA CAT TTG CAT TTT ATC CCT ATG TGG 2800       2810       2820       2830
           *         *         *         *
 TCG CTC CAG ACT TGG GAA ACT ATT CAT GAA TAT TTA TAT TGT ATG
```

CEA-(c)(SEQ ID NO:6):

```
                10                  30                  50
                 .         .         .         .         .
CAGCCGTGCTCGAAGCGTTCCTGGAGCCCAAGCTCTCCTCCACAGGTGAAGACAGGGCCA 70                  90                 110
                 .         .         .         .         .
GCAGGAGACACCATGGGGCACCTCTCAGCCCCACTTCACAGAGTGCGTGTACCCTGGCAG
            MetGlyHisLeuSerAlaProLeuHisArgValArgValProTrpGln 130                 150                 170
                 .         .         .         .         .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu
```

-continued

```
         190             210             230
          .               .               .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250             270             290
          .               .               .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310             330             350
          .               .               .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370             390             410
          .               .               .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430             450             470
          .               .               .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490             510             530
          .               .               .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550             570             590
          .               .               .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610             630             650
          .               .               .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670             690             710
          .               .               .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730             750             770
          .               .               .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790             810             830
          .               .               .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850             870             890
          .               .               .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910             930             950
          .               .               .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970             990             1010
          .               .               .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030            1050            1070
          .               .               .
ATAGTCACTGAGCTAAGTCCAGTAGTAGCAAAGCCCCAAATCAAAGCCAGCAAGACCACA
IleValThrGluLeuSerProValValAlaLysProGlnIleLysAlaSerLysThrThr 1090            1110            1130
          .               .               .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer
```

```
                                 -continued
          1150                1170                1190
            .                   .                   .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1210                1230                1250
            .                   .                   .
GGCAACACCACCCTCAGCATAAACCCTGTCAAGAGGGAGGATGCTGGGACGTATTGGTGT
GlyAsnThrThrLeuSerIleAsnProValLysArgGluAspAlaGlyThrTyrTrpCys 1270                1290                1310
            .                   .                   .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1330                1350                1370
            .                   .                   .
AATGCTCTACCACAAGAAAATGGCCTCTCACCTGGGGCCATTGCTGGCATTGTGATTGGA
AsnAlaLeuProGlnGluAsnGlyLeuSerProGlyAlaIleAlaGlyIleValIleGly 1390                1410                1430
            .                   .                   .
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450                1470                1490
            .                   .                   .
ACCGGCAGGGCAAGCGACCAGCGTGATCTCACAGAGCACAAACCCTCAGTCTCCAACCAC
ThrGlyArgAlaSerAspGlnArgAspLeuThrGluHisLysProSerValSerAsnHis 1510                1530                1550
            .                   .                   .
ACTCAGGACCACTCCAATGACCCACCTAACAAGATGAATGAAGTTACTTATTCTACCCTG
ThrGlnAspHisSerAsnAspProProAsnLysMetAsnGluValThrTyrSerThrLeu 1570                1590                1610
            .                   .                   .
AACTTTGAAGCCCAGCAACCCACACAACCAACTTCAGCCTCCCCATCCCTAACAGCCACA
AsnPheGluAlaGlnGlnProThrGlnProThrSerAlaSerProSerLeuThrAlaThr 1630                1650                1670
            .                   .                   .
GAAATAATTTATTCAGAAGTAAAAAAGCAGTAATGAAACCTGTCCTGCTCACTGCAGTGC
GluIleIleTyrSerGluValLysLysGln 1690                1710                1730
            .                   .                   .
TGATGTATTTCAAGTCTCTCACCCTCATCACTAGGAGATTCCTTTCCCCTGTAGGGTAGA 1750                1770                1790
            .                   .                   .
GGGGTGGGGACAGAAACAACTTTCTCCTACTCTTCCTTCCTAATAGGCATCTCCAGGCTG 1810                1830                1850
            .                   .                   .
CCTGGTCACTGCCCCTCTCTCAGTGTCAATAGATGAAAGTACATTGGGAGTCTGTAGGAA 1870                1890                1910
            .                   .                   .
ACCCAACCTTCTTGTCATTGAAATTTGGCAAAGCTGACTTTGGGAAAGAGGGACCAGAAC 1930                1950                1970
            .                   .                   .
TTCCCCTCCCTTCCCCTTTTCCCAACCTGGACTTGTTTTAAACTTGCCTGTTCAGAGCAC 1990                2010                2030
            .                   .                   .
TCATTCCTTCCCACCCCCAGTCCTGTCCTATCACTCTAATTCGGATTTGCCATAGCCTTG 2050                2070                2090
            .                   .                   .
AGGTTATGTCCTTTTCCATTAAGTACATGTGCCAGGAAACAGCGAGAGAGAGAAAGTAAA 2110                2130                2150
            .                   .                   .
CGGCAGTAATGCTTCTCCTATTTCTCCAAAGCCTTGTGTGAACTAGCAAAGAGAAGAAAA 2170                2190                2210
            .                   .                   .
TCAAATATATAACCAATAGTGAAATGCCACAGGTTTGTCCACTGTCAGGGTTGTCTACCT
```

```
          2230        2250         2270
           .           .            .
GTAGGATCAGGGTCTAAGCACCTTGGTGCTTAGCTAGAATACCACCTAATCCTTCTGGCA 2290        2310         2330
           .           .            .
AGCCTGTCTTCAGAGAACCCACTAGAAGCAACTAGGAAAAATCACTTGCCAAAATCCAAG 2350        2370         2390
           .           .            .
GCAATTCCTGATGGAAAATGCAAAAGCACATATATGTTTTAATATCTTTATGGGCTCTGT 2410        2430         2450
           .           .            .
TCAAGGCAGTGCTGAGAGGGAGGGGTTATAGCTTCAGGAGGGAACCAGCTTCTGATAAAC 2470        2490         2510
           .           .            .
ACAATCTGCTAGGAACTTGGGAAAGGAATCAGAGAGCTGCCCTTCAGCGATTATTTAAAT 2530        2550         2570
           .           .            .
TGTTAAAGAATACACAATTTGGGGTATTGGGATTTTTCTCCTTTTCTCTGAGACATTCCA 2590        2610         2630
           .           .            .
CCATTTTAATTTTTGTAACTGCTTATTTATGTGAAAAGGGTTATTTTTACTTAGCTTAGC 2650        2670         2690
           .           .            .
TATGTCAGCCAATCCGATTGCCTTAGGTGAAAGAAACCACCGAAATCCCTCAGGTCCCTT 2710        2730         2750
           .           .            .
GGTCAGGAGCCTCTCAAGATTTTTTTGTCAGAGGCTCCAAATAGAAAATAAGAAAAGGT 2770        2790         2810
           .           .            .
TTTCTTCATTCATGGCTAGAGCTAGATTTAACTCAGTTTCTAGGCACCTCAGACCAATCA 2830        2850         2870
           .           .            .
TCAACTACCATTCTATTCCATGTTTGCACCTGTGCATTTTCTGTTTGCCCCCATTCACTT 2890        2910         2930
           .           .            .
TGTCAGGAAACCTTGGCCTCTGCTAAGGTGTATTTGGTCCTTGAGAAGTGGGAGCACCCT 2950        2970         2990
           .           .            .
ACAGGGACACTATCACTCATGCTGGTGGCATTGTTTACAGCTAGAAAGCTGCACTGGTGC 3010        3030         3050
           .           .            .
TAATGCCCCTTGGGAAATGGGGCTGTGAGGAGGAGGATTATAACTTAGGCCTAGCCTCTT 3070        3090         3110
           .           .            .
TTAACAGCCTCTGAAATTTATCTTTTCTTCTATGGGGTCTATAAATGTATCTTATAATAA 3130        3150         3170
           .           .            .
AAAGGAAGGACAGGAGGAAGACAGGCAAATGTACTTCTCACCCAGTCTTCTACACAGATG 3190        3210         3230
           .           .            .
GAATCTCTTTGGGGCTAAGAGAAAGGTTTTATTCTATATTGCTTACCTGATCTCATGTTA 3250        3270         3290
           .           .            .
GGCCTAAGAGGCTTTCTCCAGGAGGATTAGCTTGGAGTTCTCTATACTCAGGTACCTCTT 3310        3330         3350
           .           .            .
TCAGGGTTTTCTAACCCTGACACGGACTGTGCATACTTTCCCTCATCCATGCTGTGCTGT 3370        3390         3410
           .           .            .
GTTATTTAATTTTTCCTGGCTAAGATCATGTCTGAATTATGTATGAAAATTATTCTATGT
```

-continued

```
     3430           3450
       .              .
TTTTATAATAAAAATAATATATCAGACATCGAAAAAAAAAA
```

CEA-(d)(SEQ ID NO:7):

```
       10             30             50
        .              .              .
CCGGGGGACACGCAGGGCCAACAGTCACAGCAGCCCTGACCAGAGCATTCCTGGAGCTCAAG 70             90            110
        .              .              .
CTCTCTACAAAGAGGTGGACAGAGAAGACAGCAGAGACCATGGGACCCCCCTCAGCCCCT
                                      MetGlyProProSerAlaPro 130            150            170
        .              .              .
CCCTGCAGATTGCATGTCCCCTGGAAGGAGGTCCTGCTCACAGCCTCACTTCTAACCTTC
ProCysArgLeuHisValProTrpLysGluValLeuLeuThrAlaSerLeuLeuThrPhe 190            210            230
        .              .              .
TGGAACCCCACCCACCACTGCCAAGCTCACTATTGAATCCACGCCATTCAATGTCGCAGAG
TrpAsnProProThrThrAlaLysLeuThrIleGluSerThrProPheAsnValAlaGlu 250            270            290
        .              .              .
GGGAAGGAGGTTCTTCTACTCGCCCACAACCTGCCCCAGAATCGTATTGGTTACAGCTGG
GlyLysGluValLeuLeuLeuAlaHisAsnLeuProGlnAsnArgIleGlyTyrSerTrp 310            330            350
        .              .              .
TACAAAGGCGAAAGAGTGGATGGCAACAGTCTAATTGTAGGATATGTAATAGGAACTCAA
TyrLysGlyGluArgValAspGlyAsnSerLeuIleValGlyTyrValIleGlyThrGln 370            390            410
        .              .              .
CAAGCTACCCCAGGGCCCGCATACAGTGGTCGAGAGACAATATACCCCAATGCATCCCTG
GlnAlaThrProGlyProAlaTyrSerGlyArgGluThrIleTyrProAsnAlaSerLeu 430            450            470
        .              .              .
CTGATCCAGAACGTCACCCAGAATGACACAGGATTCTACACCCTACAAGTCATAAAGTCA
LeuIleGlnAsnValThrGlnAsnAspThrGlyPheTyrThrLeuGlnValIleLysSer 490            510            530
        .              .              .
GATCTTGTGAATGAAGAAGCAACCGGACAGTTCCATGTATACCCGGAGCTGCCCAAGCCC
AspLeuValAsnGluGluAlaThrGlyGlnPheHisValTyrProGluLeuProLysPro 550            570            590
        .              .              .
TCCATCTCCAGCAACAACTCCAACCCCGTGGAGGACAAGGATGCTGTGGCCTTCACCTGT
SerIleSerSerAsnAsnSerAsnProValGluAspLysAspAlaValAlaPheThrCys 610            630            650
        .              .              .
GAACCTGAGGTTCAGAACACAACCTACCTGTGGTGGGTAAATGGTCAGAGCCTCCCGGTC
GluProGluValGlnAsnThrThrTyrLeuTrpTrpValAsnGlyGlnSerLeuProVal 670            690            710
        .              .              .
AGTCCCAGGCTGCAGCTGTCCAATGGCAACAGGACCCTCACTCTACTCAGCGTCAAAAGG
SerProArgLeuGlnLeuSerAsnGlyAsnArgThrLeuThrLeuLeuSerValLysArg 730            750            770
        .              .              .
AACGATGCAGGATCGTATGAATGTGAAATACAGAACCCAGCGAGTGCCAACCGCAGTGAC
AsnAspAlaGlySerTyrGluCysGluIleGlnAsnProAlaSerAlaAsnArgSerAsp 790            810            830
        .              .              .
CCAGTCACCCTGAATGTCCTCTATGGCCCAGATGGCCCCACCATTTCCCCCTCAAAGGCC
ProValThrLeuAsnValLeuTyrGlyProAspGlyProThrIleSerProSerLysAla 850            870            890
        .              .              .
AATTACCGTCCAGGGGAAAATCTGAACCTCTCCTGCCACGCAGCCTCTAACCCACCTGCA
AsnTyrArgProGlyGluAsnLeuAsnLeuSerCysHisAlaAlaSerAsnProProAla
```

```
           910              930             950
            .                .               .
CAGTACTCTTGGTTTATCAATGGGACGTTCCAGCAATCCACACAAGAGCTCTTTATCCCC
GlnTyrSerTrpPheIleAsnGlyThrPheGlnGlnSerThrGlnGluLeuPheIlePro 970              990            1010
            .                .               .
AACATCACTGTGAATAATAGCGGATCCTATATGTGCCAAGCCCATAACTCAGCCACTGGC
AsnIleThrValAsnAsnSerGlySerTyrMetCysGlnAlaHisAsnSerAlaThrGly 1030             1050            1070
            .                .               .
CTCAATAGGACCACAGTCACGATGATCACAGTCTCTGGAAGTGCTCCTGTCCTCTCAGCT
LeuAsnArgThrThrValThrMetIleThrValSerGlySerAlaProValLeuSerAla 1090             1110            1130
            .                .               .
GTGGCCACCGTCGGCATCACGATTGGAGTGCTGGCCAGGGTGGCTCTGATATAGCAGCCC
ValAlaThrValGlyIleThrIleGlyValLeuAlaArgValAlaLeuIleEnd 1150       1160        1170       1180       1190
           .          .           .          .          .
      TGG TGT ATT TTC GAT ATT TCA GGA AGA CTG GCA GAT TGG ACC AGA CCC TGA ATT CTT
1200        1210         1220        1230       1240       1250
  .           .            .           .          .          .
      CTA GCT CCT CCA ATC CCA TTT TAT CCC ATG AAC CCA CTA AAA ACA AGG TCT GCT CTG 1260        1270        1280       1290       1300       1310
           .           .           .          .          .          .
      CTC CTG AAG CCC TAT ATG CTG GAG ATG GAC AAC TCA ATG AAA ATT TAA AAG AAA AAC 1320        1330       1340       1350       1360       1370
             .           .          .          .          .          .
        CCT CAG GCC TGA GGT GTG TGC CAC TCA GAG ACT TCA CCT AAC TAG AGA CAG GCA AAC 1380       1390       1400       1410       1420
               .          .          .          .          .
         TGC AAA CCA nnC CTC TTT CGC TTG GCA GGA TGA TGG TGT CAT TAG TAT TTC ACA AGA 1430       1440       1450       1460       1470       1480
           .          .          .          .          .          .
      AGT AGC TTC AGA GGG TAA CTT AAC AGA GTA TCA GAT CTA TCT TGT CAA TCC CAA CGT 1490       1500       1510       1520       1530       1540
           .          .          .          .          .          .
      TTT ACA TAA AAT AAG CGA TCC TTT AGT GCA CCC AGT GAC TGA CAT TAG CAG CAT CTT 1550       1560       1570       1580       1590
             .          .          .          .          .
        TAA CAC AGC CGT GTG TTC AAG TGT ACA GTG GTC CTT TTC AGA GTT GGn nnT ACT CCA 1600        1610       1620       1630       1640       1650
  .           .          .          .          .          .
      ACT GAA ATG TTA AGG AAG AAG ATA GAT CCA ATT AAA AAA AAT TAA AAC CAA TTT AAA 1660       1670       1680       1690       1700       1710
           .          .          .          .          .          .
      AAA AAA AAA GAA CAC AGG AGA TTC CAG TCT ACT TGA GTT AGC ATA ATA CAG AAG TCC 1720       1730       1740       1750       1760
             .          .          .          .          .
        CCT CTA CTT TAA CTT TTA CAA AAA AGT AAC CTG AAC TAA TCT GAT GTT AAC CAA TGT
1770        1780       1790       1800       1810       1820
  .           .          .          .          .          .
      ATT TAT TTG TCT GGT TCT GTT TCC TTG TTC CAA TTT GAC AAA ACC CAC TGT TCT TGT 1830       1840       1850       1860       1870       1880
           .          .          .          .          .          .
      ATT GTA TTG CCC AGG GGG AGC TAT CAC TGT ACT TGT AGA GTG GTG CTG CTT TAA GTT 1890       1900       1910       1920       1930       1940
           .          .          .          .          .          .
      CAT AAA TCA CAA ATA AAA GCC AAT TAG CTC TAT AAC TAA AAA AAA AAA AAA AAA 1950       1960
             .          .
        AAA AAA AAA AAA AAA AAA AAA AAA
```

Figure 1B:
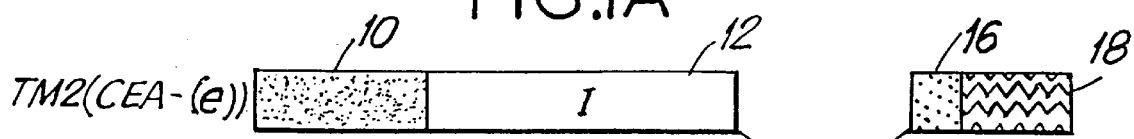
Figure 1C:
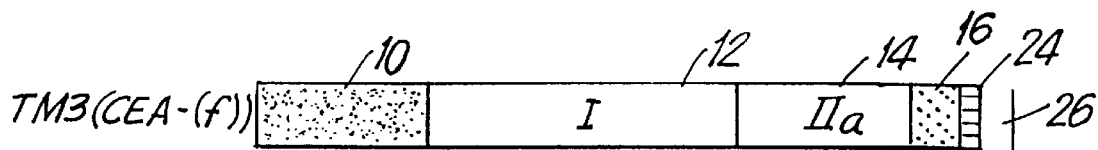
Figure 1D:
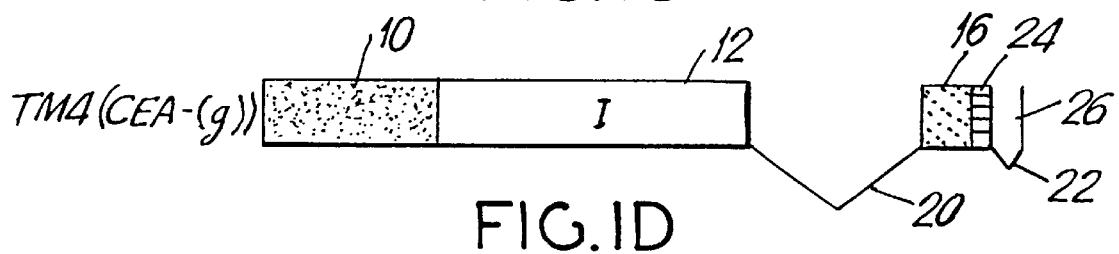

A schematic relationship of the transmembrane CEA's, namely TM-1 (CEA-(c)), TM-2 (CEA-(e)), TM-3 (CEA-(f)) and TM-4 (CEA-(g)) is depicted in FIG. 1:

Assuming TM-1 is composed of five sections as depicted in FIG. 1, namely 10, 12, 14, 16 and 18, TM-2 differs from TM-1 in that the 100 amino acid (100 AA) section 14 is deleted and at splice point 20 betweeen sections 12 and 16, surprisingly an extra amino acid, namely Asp occurs.

TM-3 is the same as TM-1 except that section 18 is truncated at splice point 22, i.e., a section of 70 amino acids is deleted and results in a new section made up of subsections 24+26. Surprisingly, however, six new amino acids (section 26) occur. Another example of formation of a novel amino acid sequence resulting from a deletion of nucleic acid sequence is for platelet derived growth factor-A.

TM-4 is the same as TM-2 up until the end of subsection 24.

Subsection 24 is contained in section 18 of TM-1 and TM-2, but is not depicted in FIG. 1 for TM-1 and TM-2.

Some CEA epitopes are unique. These are the epitopes which have been useful for distinguishing the various CEA-like antigens immunologically. Peptide epitopes are defined by the linear amino acid sequence of the antigen and/or features resulting from protein folding. The information required for protein folding is encoded in the primary amino acid sequence. Therefore, antigenic differences ultimately result from differences in the primary structure of the different CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected for each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from E. coli including col E1, pCR1, pBR322, pMB89 and their derivatives, wider host range plasmids, e.g., RP4, and phage DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the $2\mu$ plasmid or derivatives thereof. Useful hosts may include bacterial hosts such as strains of E. coli, such as E. coli HB 101, E. coli X1776, E. coli X2282, E. coli MRC1 and strains of Pseudomonas, Bacillus subtilis, Bacillus stearothermophilus and other E. coli, bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the PstI site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoRI site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop codons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example, dA-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucleotides which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), the major operator and promoter regions of phage λ ($O_L P_L$ and $O_R P'_R$), the control region of Filamenteous single-stranded DNA phages, or other sequences which control the expression of genes of prokaryotic or eukaryotic cells and their viruses. Therefore, to improve the production of a particular polypeptide in an appropriate host, the gene coding for that polypeptide may be selected and removed from a recombinant nucleic acid molecule containing it and reinserted into a recombinant nucleic acid molecule closer or in a more appropriate relationship to its former expression control sequence or under the control of one of the above described expression control sequences. Such methods are known in the art.

As used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53–61 (1977) and N. E. Murray et al, "Molecular Cloning of the DNA Ligase Gene From Bacteriophage T4", *J. Mol. Biol.*, 132, pp. 493–505 (1979)) and the recombinant DNA molecule recircularized by incubation with DNA ligase. The desired recombinant phage is then selected as before and used to lysogenize a host strain of E. coli.

Particularly useful λ cloning vehicles contain a temperature-sensitive mutation in the repression gene cI and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those coded for by the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:

(1) the polypeptides expressed by the above described cells,
(2) polypeptides prepared by synthetic means,
(3) fragments of polypeptides (1) or (2) above, such fragments produced by synthesis of amino acids or by digestion or cleavage.

Regarding the synthetic peptides according to the invention, chemical synthesis of peptides is described in the following publications: S. B. H. Kent, *Biomedical Polymers*, eds. Goldberg, E. P. and Nakajima, A. (Academic Press, New York), 213–242, (1980); A. R. Mitchell, S. B. H. Kent, M. Engelhard and R. B. Merrifield, *J. Org. Chem.*, 43, 2845–2852, (1978); J. P. Tam, T.-W. Wong, M. Riemen, F.-S. Tjoeng and R. B. Merrifield, *Tet. Letters*, 4033–4036, (1979); S. Mojsov, A. R. Mitchell and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.) 1981.

In the Merrifield solid phase procedure, the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by making for 10 minutes at room temperature with 5% (v/v) diisopropylethylamine (or other hindered base) in methylene chloride;

(c) washed with methylene chloride;

(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysine) or other protecting groups commonly used in peptide synthesis;

(e) the activated amino acid is reacted with the peptide-resin for two hours at room temperature, resulting in addition of the new amino acid to the end of the growing peptide chain;

(f) the peptide-resin is washed with methylene chloride;

(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;

(h) the peptide-resin is washed with methylene chloride;

(i) steps (a) through (h) are repeated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites inmmediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide; asparaginyl-glycine bonds are cleaved by hydroxylamine.

The present invention has the following advantages:

(1) The nucleic acids coding for TM-1, TM-2 and TM-3 can be used as probes to isolate other members of the CEA gene family.

(2) The nucleic acids coding for TM-1, TM-2 and TM-3 can be used to derive oligonucleotide probes to determine the expression of TM-1, TM-2, TM-3 and other CEA genes in various tumor types.

(3) TM-1, TM-2, TM-3 and TM-4 nucleotide sequences can be used to predict the primary amino acid sequence of the protein for production of synthetic peptides.

(4) Synthetic peptides derived from the above sequences can be used to produce sequence-specific antibodies.

(5) Imnunoassays for each member of the CEA antigen family can be produced with these sequence-specific antibodies and synthetic peptides.

(6) The aforementioned immunoassays can be used as diagnostics for different types of cancer if it is determined that different members of the CEA family are clinically useful markers for different types of cancer.

Peptides according to the present invention can be labelled by conventional means using radioactive moieties (e.g., $^{125}$I), enzymes, dyes and fluorescent compounds, just to name a few.

Several possible configurations for immunoassays according to the present invention can be used. The readout systems capable of being employed in these assays are numerous and non-limiting examples of such systems include fluorescent and calorimetric enzyme systems, radioisotopic labelling and detection and chemiluminescent systems. Two examples of immunoassay methods are as follows:

(1) An enzyme linked immunoassay (ELISA) using an antibody preparation according to the present invention (including Fab or F(ab)' fragments derived therefrom) to a solid phase (such as a microtiter plate or latex beads) is attached a purified antibody of a specificity other than that which is conjugated to the enzyme. This solid phase antibody is contacted with the sample containing CEA antigen family members. After washing, the solid phase antibody-antigen complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of antigen in the sample.

(2) A competitive fluorometric immunoassay using fluorescently labelled peptide or synthetic peptides of the sequences for TM-2, TM-2, TM-3 and TM-4. In this example, the purified peptide expressed by cells or synthetic peptides thereof are fluorescently labelled. To a solid phase is attached a purified antibody. This solid phase is then contacted with sample containing CEA antigen family members to which has been added fluorescent peptide probe. After binding, excess probe is washed away the amount of bound probe is quantitated. The amount of bound fluorescent probe will be inversely proportional to the amount of antigen in the sample.

In the nucleic acid hybridization method according to the present invention, the nucleic acid probe is conjugated with a label, for example, an enzyme, a fluorophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods for these last two techniques are described by D. Gillespie and J. Bresser, "mRNA Immobilization in NaI: Quick Blots", *Biotechniques*, 184–192, November/December 1983 and J. Lawrence and R. Singer, "Intracellular Localization of Messenger RNAs for Cytosketal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The invention further provides a pharmaceutical composition containing as an active ingredient a complex of the invention in the form of a sterile and/or physiologically isotonic aqueous solution.

For parenteral administration, solutions and emulsions containing as an active ingredient the complex of the invention should be sterile and, if appropriate, blood-isotonic.

It is envisaged that the active complex will be administered perorally, parenterally (for example, intramuscularly, intraperitoneally, or intravenously), rectally or locally.

EXAMPLE 1

Preparation of cDNA in pcE22 Which Codes for TM2-CEA [CEA-(e)]

Example 1a

RNA Preparation

Messenger RNA was prepared by the proteinase K extraction method of J. Favolaro, R. Treisman and R. Kamen, *Methods in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately $3 \times 10^8$ cells of transfectant 23.411 (ATCC No. CRL 9731, deposited with the ATCC on Jun. 1, 1988), that expresses TM-1, TM-2, TM-3 and TM-4, Kamarck et al, *Proc. Natl. Acad. Sci., USA*, 84, 5350–5354, August 1987, were harvested from roller bottles after late logarithmic growth. Cells were lysed by homogenization in an ice-cold solution of 140 mM NaCl, 1.5 mM $MgCl_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centrifugation of the homogenate at 12,000×g for 20 minutes. The cytoplasmic fraction was mixed with an equal volume of 0.2M Tris-HCl, pH 7.8, 25 mM EDTA, 0.3M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obrtained by ethanol precipitation of the separated aqueous phase. Total RNA was enriched by passage in 0.5M NaCl, 10 mM Tris-HCl, pH 7.8, 0.1% sarcosyl through an oligo dT(12-18) cellulose column. After washing, bound RNA was eluted in the same solution without sodium chloride.

Example 1b

Reverse Transcription of mRNA

Ten micrograms of poly A+ RNA were primed for reverse transcription with oligo dT(12-18) and $pdN_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

Example 1c

Cloning of pcE22 (plasmid cDNA E22)

```
Synthetic DNA 5'  pCCCGGG      3'   (SEQ ID NO:14)
linkers      3'   GGGCCCTTAA 5'
``` were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the 23.411 cell line, the size of the CEA-related mRNA was estimated at 3.6 kb. Therefore, cDNA fragments between 2 and 4 kb were recovered from gel slices and fragments were ethanol precipitated. After resuspension of cDNA in TE, EcoRI-cleaved lambada gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained ofter in vitro packaging and infection of *E. coli* host NM514.

Example 1d

Screening of Recombinant Library

Five hundred thousand packaged lambda particles were plated on lawns of *E. coli* NM514 and replicate patterns were lifted onto nitrocellulose sheets as described by W. D. Benton and R. W. Davis, *Science* 196, 180–182, (1977). Positive phage were selected by hybridization with $^{32}P$-labeled LV7 cDNA insert probe that contained a domain repeated amoung various CEA family members. By multiple rounds of screening. Phage from individual plaques were amplified and titered, and these were used to prepare small quantities of recombinant phage DNA.

Example 1e

DNA Manipulation

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci., U.S.A.*, 74, 5463–5467, (1977). The nucleic acid and translated sequence for cDNA in pcE22 is given hereinabove (TM-2 (CEA-(e)).

EXAMPLE 2

Preparation of cDNA in pcHT-6 Which Particlally Codes for TM3-CEA [CEA-(f)]

Example 2a

RNA Preparation

Messenger RNA was prepared by the proteinase K extraction method of J. Favolaro, R. Treisman and R. Kamen, *Methods in Enzymology*, 65 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately 3×10⁸ cells of HT-29 tumor cells (ATCC HTB38) were harvested form roller bottles after late logarithmic growth. Cells were lysed by homogenization in an ice-cold solution of 140 mM NaCl, 1.5 mM MgCl₂, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centrifugation of the homogenate at 12,000×g for 20 minutes. The cytoplasmic fraction was mixed with an equal volume of 0.2M Tris-Hcl, pH 7.8, 25 mM EDTA, 0.3M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obrtained by ethanol precipitation of the separated aqueous phase. Total RNA was enriched by passage in 0.5M NaCl, 10 mM Tris-HCl, pH 7.8, 0.1% sarcosyl through an oligo dT(12-18) cellulose column. After washing, bound RNA was eluted in the same solution without sodium chloride.

Example 2b

Reverse Transcription of mRNA

Ten micrograms of HT-29 poly A+ RNA were primed for reverse transcription with oligo dT(12-18) and pdN₆ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

Example 2c

Cloning of pcHT-6 (plasmid cDNA HT-6)

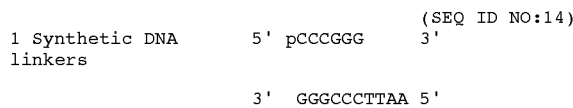

were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the HT-29 cell line, the size of the CEA-related mRNA was estimated at 2.2 kb. Therefore, cDNA fragments between 2 and 3 kb were recovered from gel slices and fragments were ethanol precipitated. After resuspension of cDNA in TE, EcoRI-cleaved lambada gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained ofter in vitro packaging and infection of *E. coli* host NM514.

Example 2d

Screening of Recombinant Library

Five hundred thousand packaged lambda particles were plated on lawns of *E. coli* NM514 and replicate patterns were lifted onto nitrocellulose sheets as described by W. D. Benton and R. W. Davis, *Science*, 196, 180–182, (1977). Positive phage were selected by hybridization with ³²P-labeled LV7 cDNA insert probe that contained a domain repeated amoung various CEA family members. By multiple rounds of screening. Phage from individual plaques were amplified and titered, and these were used to prepare small quantities of recombinant phage DNA.

Example 2e

DNA Manipulation

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci., U.S.A.*, 74, 5463–5467, (1977). The nucleic acid and translated sequence for cDNA in HT-6 not complete at the 5' end of its coding region, but the nucleotide sequenece and restriction map of the HT-6 insert indicates that it is related to nucleic acid sequences of cDNA clones coding for CEA-(c) and CEA-(e). The nucleotide sequence of HT-6 insert differs from these clones at only nucleotide position 1463 to 1515 and 1676 to 2429 of the CEA-(c) cDNA. It is inferred from this result that the pcHT-6 insert is a partial coding sequence for CEA-(f) and the presumed nucleic acid and translated sequence of CEA-(f) is given hereinabove (TM-3 (CEA-(f))

EXAMPLE 3

Preparation of cDNA Which Codes for TM4-CEA [CEA-(g)]

Example 3a

RNA Preparation

Messenger MRNA is prepared by the proteinase K extraction method of J. Favolaro, R. Treisman and R. Kamen, *Methos in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately 3×10⁸ cells of transfectant 23.411 or tumor cell line HT-29 (ATCC HTB 38) are harvested from roller bottles after late logarithmic growth. Cells are lysed by homogenization in an ice-cold solution of 140 mM NaCl, 1.5 mM MgCl₂, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei are separated by centrifugation of the homogenate at 12,000×g for 20 minutes. The cytoplasmic fraction is mixed with an equal volume of 0.2M Tris-Hcl, pH 7.8, 25 mM EDTA, 0.3M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids are obtained by ethanol precipitation of the separated aqueous phase. Total RNA is enriched by passage in 0.5M NaCl, 10 mM Tris-HCl, pH 7.8, 0.1% sarcosyl through an oligo dT(12-18) cellulose column. After washing, bound RNA is eluted in the same solution without sodium chloride.

Example 3b

Reverse Transcription of mRNA

Ten micrograms of 23.411 or HT 29 poly A+ RNA are primed for reverse transcription with oligo dT(12-18) and pdN₆ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids is replaced with the second complementary strand by treatment with RNase H, *E. coli* DNA polymerase I and *E. coli* DNA ligase at 12° C. and 22° C. for 1.5 hours each. Molecular ends are polished by treatment with T4 DNA polymerase. cDNA is phenol/chloroform extracted and purified over a "SEPHADEX G-50" spun column prepared in 10 mM Tris-HCl, pH 7.8, 1 mM EDTA (TE).

Example 3c

Cloning of cDNA for CEA-(g)

```
Synthetic DNA linkers   5' pCCCGGG      3'

3'   GGGCCCTTAA 5'  (SEQ ID
                                             NO: 14)
``` are attached to the ends of cDNA by blunt end ligation with excess T4 DNA ligase. Excess linkers are removed by chromatography through "SEPHADEX G-50" (medium) in TE, and by fractionation on 0.8% low melting agarose gel. Based on Northern blot analysis of poly A+ RNA of the 23.411 and HT-29 cell lines, the size of the CEA-related mRNA is estimated at 1.7 kb. Therefore, cDNA fragments between 1 and 2 kb are recovered from gel slices and fragments are ethanol precipitated. After resuspension of cDNA in TE, EcoRI-cleaved lambda gt10 arms are added to cDNA at an estimated molar ratio of 1:1. Ligation proceeds at 7° C. for 2 days in the presence of T4 DNA ligase. Aliquots of the ligation reaction are added to commercially-obtained packaging mix (Stratagene, San Diego, Calif., U.S.A.). Phage particles are obtained after in vitro packaging and infection of *E. coli* host NM514.

Example 3d

Screening of Recombinant Library

Five hundred thousand to one million packaged lambda particles are plated on lawns of *E. coli* NM514 and replicate patterns are lifted onto nitrocellulose sheets as described by W. D. Benton and R. W. Davis, *Science*, 196, 180–182, (1977). Positive phage are selected by hybridization with ³²P-labeled LV7 cDNA insert probe that contained a domain repeated amoung various CEA family members. By this selection method, positive phage are obtained after multiple rounds of screening. Phage from individual plaques are amplified and titered, and these are used to prepare small quantities of recombinant phage DNA.

Example 3e

DNA Manipulation

Phage DNA is prepared according to T. Maniatis, E. Fritsch and J. Sambrook, *Molecular Cloning, A Laboratory Manual*, Cold Spring Harbor, (1982). DNA segments are isolated from low melting agarose gels and inserted for subcloning into Bluescript plasmid vectors (Stratagene, San Diego, Calif., U.S.A.). DNA sequencing is performed by the dideoxy termination method of F. Sanger, S. Nicklen and A. Coulson, *Proc. Natl. Acad. Sci., U.S.A.*, 74, 5463–5467, (1977). The nucleotide and translated sequence for a cDNA coding for CEA-(g) is given hereinabove (TM-4 (CEA-(g)).

EXAMPLE 4

Screening of a KG-1 cDNA Library with ³²p-labelled CEA Probe, LV7 (CEA-(A))

A segment of cDNA coding for a portion of carcinoembryonic antigen [LV7 or CEA-(a)] was radiolabelled by random priming and used to detect homologous sequences on filter replicas of a commercial cDNA library prepared from KG-1 cells in bacteriophage vector λ gt11 (Clontech Laboratories, Inc., Palo Alto, Calif., U.S.A.). Hybridizations were performed at 68° C. in 2× SSSPE (1× SSPE—0.15M NaCl, 0.01M sodium phosphate and 1 mM EDTA, pH 7), 5× Denhardt's solution and 100 μg of denatured salmon sperm DNA per ml, and post-hybridization washes were in 0.2× SSC, 0.25% sodium dodecyl sulfate.

Positive phage were picked, rescreened to homogeneity, and amplified for production of DNA. cDNA inserts were excised from phage DNA with EcoRI endonuclease and subcloned into the EcoRI site of the plasmid vector pBluescript KS. DNA sequencing on double-stranded DNA was by the method of Sanger et al, supra. The sequences of two different inserts from the KG-1 cDNA library are shown below:

```
pcKGCEA1(SEQ ID NO:8):

1   acagcacagctgacagccgtactcaggaagcttctggatcctaggcttatctccacagag   60

61   gagaacacacaagcagcagagaccatggggcccctctcagcccctccctgcacacacctc  120
                                MetGlyProLeuSerAlaProProCysThrHisLeu 121   atcacttggaaggggtcctgctcacagcatcacttttaaacttctggaatccgcccaca  180
      IleThrTrpLysGlyValLeuLeuThrAlaSerLeuLeuAsnPheTrpAsnProProThr 181   actgcccaagtcacgattgaagcccagccacccaaagtttctgaggggaaggatgttctt  240
      ThrAlaGlnValThrIleGluAlaGlnProProLysValSerGluGlyLysAspValLeu 241   ctacttgtccacaatttgccccagaatcttgctggctacatttggtacaaagggcaaatg  300
      LeuLeuValHisASnLeuProGlnAsnLeuAlaGlyTyrIleTrpTyrLysGlyGlnMet 301   acatacgtctaccattacattacatcatatgtagtagacggtcaaagaattatatatggg  360
      ThrTyrValTyrHisTyrIleThrSerTyrValValAspGlyGlnArgIleIleTyrGly 361   cctgcatacagtggaagagaaagagtatattccaatgcatccctgctgatccagaatgtc  420
      ProAlaTyrSerGlyArgGluArgValTyrSerAsnAlaSerLeuLeuIleGlnAsnVal
```

-continued

```
 421  acgcaggaggatgcaggatcctacaccttacacatcataaagcgacgcgatgggactgga   480
      ThrGlnGluAspAlaGlySerTyrThrLeuHisIleIleLysArgArgAspGlyThrGly 481  ggagtaactggacatttcaccttcaccttacacctggagactcccaagccctccatctcc   540
      GlyValThrGlyHisPheThrPheThrLeuHisLeuGluThrProLysProSerIleSer 541  agcagcaacttaaatcccaggqaggccatggaggctgtgatcttaacctgtgatcctgcg   600
      SerSerAsnLeuAsnProArgGluAlaMetGluAlaValIleLeuThrCysAspProAla 601  actccagccgcaagctaccagtggtggatgaatggtcagagcctccctatgactcacagg   660
      ThrProAlaAlaSerTyrGlnTrpTrpMetAsnGlyGlnSerLeuProMetThrHisArg 661  ttgcagctgtccaaaaccaacaggaccctctttatatttggtgtcacaaagtatattgca   720
      LeuGlnLeuSerLysThrAsnArgThrLeuPheIlePheGlyValThrLysTyrIleAla 721  ggacccctatgaatgtgaaatacggaacccagtgagtgccagccgcagtgacccagtcacc   780
      GlyProTyrGluCysGluIleArgAsnProValSerAlaSerArgSerAspProValThr 781  ctgaatctcctcccaaagctgtccaagccctacatcacaatcaacaacttaaaccccaga   840
      LeuAsnLeuLeuProLysLeuSerLysProTyrIleThrIleAsnAsnLeuAsnProArg 841  gagaataaggatgtcttaaccttcacctgtgaacctaagagtgagaactacacctacatt   900
      GluAsnLysAspValLeuThrPheThrCysGluProLysSerGluAsnTyrThrTyrIle 901  tggtggctaaatggtcagagcctccctgtcagtcccagggtaaagcgacccattgaaaac   960
      TrpTrpLeuAsnGlyGlnSerLeuProValSerProArgValLysArgProIleGluAsn 961  aggatcctcattctacccaatgtcacgagaaatgaaacaggaccttatcaatgtgaaata  1020
      ArgIleLeuIleLeuProAsnValThrArgAsnGluThrGlyProTyrGlnCysGluIle 1021  cgggaccgatatggtggcatccgcagtgacccagtcaccctgaatgtcctctatggtcca  1080
      ArgAspArgTyrGlyGlyIleArgSerAspProValThrLeuAsnValLeuTyrGlyPro 1081  gacctccccagcatttacccttcattcacctattaccgttcaggagaaaacctctacttt  1140
      AspLeuProSerIleTyrProSerPheThrTyrTyrArgSerGlyGluAsnLeuTyrPhe 1141  tcctgcttcggtgagtctaacccacgggcacaatattcttggacaattaatgggaagttt  1200
      SerCysPheGlyGluSerAsnProArgAlaGlnTyrSerTrpThrIleAsnGlyLysPhe 1201  cagctatcaggacaaaagctctctatcccccaataactacaaagcatagtgggctctat   1260
      GlnLeuSerGlyGlnLysLeuSerIleProGlnIleThrThrLysHisSerGlyLeuTyr 1261  gcttgctctgttcgtaactcagccactggcaaggaaagctccaaatccatcacagtcaaa  1320
      AlaCysSerValArgAsnSerAlaThrGlyLysGluSerSerLysSerIleThrValLys 1321  gtctctgactggatattaccctgaattctactagttcctccaattccatttctcccatg   1380
      ValSerAspTrpIleLeuProEnd 1381  gaatcacgaagagcaagacccactctgttccagaagccctataatctggaggtggacaac  1440

1441  tcgatgtaaatttcatgggaaaaccttgtacctgacatgtgagccactcagaactcacc   1500

1501  aaaatgttcgacaccataacaacagctactcaaactgtaaaccaggataagaagttgatg  1560

1561  acttcacactgtggacagttttcaaagatgtcataacaagactccccatcatgacaagg   1620

1621  ctccaccctctactgtctgctcatgcctgcctctttcacttggcaggataatgcagtcat  1680

1681  tagaatttcacatgtagtagcttctgagggtaacaacagagtgtcagatatgtcatctca  1740

1741  acctcaaacttttacgtaacatctcagggaaatgtggctctctccatcttgcatacaggg  1800

1801  ctcccaatagaaatgaacacagagatattgcctgtgtgtttcagagaagatggtttcta  1860

1861  taaagagtaggaaagctgaaattatagtagagtctcctttaaatgcacattgtgtggatg  1920

1921  gctctcaccatttcctaagagatacagtgtaaaaacgtgacagtaatactgattctagca  1980

1981  gaataaacatgtaccacatttgcaaaaaa                                 2010
```

-continued pcKGCEA2(SEQ ID NO:9):

```
   1 gggtggatcctaggctcatctccatagggggagaacacacatacagcagagaccatggga    59
                                                            MetGly
  60 cccctctcagcccctccctgcactcagcacatcacctggaaggggctcctgctcacagca   119
     ProLeuSerAlaProProCysThrGlnHisIleThrTrpLysGlyLeuLeuLeuThrAla
 120 tcacttttaaacttctggaacctgcccaccactgcccaagtaataattgaagcccagcca   179
     SerLeuLeuAsnPheTrpAsnLeuProThrThrAlaGlnValIleIleGluAlaGlnPro
 180 cccaaagtttctgaggggaaggatgttcttctacttgtccacaatttgccccagaatctt   239
     ProLysValSerGluGlyLysAspValLeuLeuLeuValHisAsnLeuProGlnAsnLeu
 240 actggctacatctggtacaaagggcaaatgacggacctctaccattacattacatcatat   299
     ThrGlyTyrIleTrpTyrLysGlyGlnMetThrAspLeuTyrHisTyrIleThrSerTyr
 300 gtagtagacggtcaaattatatatgggcctgcctacagtggacgagaaacagtatattcc   359
     ValValAspGlyGlnIleIleTyrGlyProAlaTyrSerGlyArgGluThrValTyrSer
 360 aatgcatccctgctgatccagaatgtcacacaggaggatgcaggatcctacaccttacac   419
     AsnAlaSerLeuLeuIleGlnAsnValThrGlnGluAspAlaGlySerTyrThrLeuHis
 420 atcataaagcgaggcgatgggactggaggagtaactggatatttcactgtcaccttatac   479
     IleIleLysArgGlyAspGlyThrGlyGlyValThrGlyTyrPheThrValThrLeuTyr
 480 tcggagactcccaagcgctccatctccagcagcaacttaaaccccagggaggtcatggag   539
     SerGluThrProLysArgSerIleSerSerSerAsnLeuAsnProArgGluValMetGlu
 540 gctgtgcgcttaatctgtgatcctgagactccggatgcaagctacctgtggttgctgaat   599
     AlaValArgLeuIleCysAspProGluThrProAspAlaSerTyrLeuTrpLeuLeuAsn
 600 ggtcagaacctccctatgactcacaggttgcagctgtccaaaaccaacaggaccctctat   659
     GlyGlnAsnLeuProMetThrHisArgLeuGlnLeuSerLysThrAsnArgThrLeuTyr
 660 ctatttggtgtcacaaagtatattgcagggccctatgaatgtgaaatacggaggggagtg   719
     LeuPheGlyValThrLysTyrIleAlaGlyProTyrGluCysGluIleArgArgGlyVal
 720 agtgccagccgcagtgacccagtcaccctgaatctcctcccgaagctgcccatgccttac   779
     SerAlaSerArgSerAspProValThrLeuAsnLeuLeuProLysLeuProMetProTyr
 780 atcaccatcaacaacttaaaccccagggagaagaaggatgtgttagccttcacctgtgaa   839
     IleThrIleAsnAsnLeuAsnProArgGluLysLysAspValLeuAlaPheThrCysGlu
 840 cctaagagtcggaactacacctacatttggtggctaaatggtcagagcctcccggtcagt   899
     ProLysSerArgAsnTyrThrTyrIleTrpTrpLeuAsnGlyGlnSerLeuProValSer
 900 ccgagggtaaagcgacccattgaaaacaggatactcattctacccagtgtcacgagaaat   959
     ProArgValLysArgProIleGluAsnArgIleLeuIleLeuProSerValThrArgAsn
 960 gaaacaggaccctatcaatgtgaaatacgggaccgatatggtggcatccgcagtaaccca  1019
     GluThrGlyProTyrGlnCysGluIleArgAspArgTyrGlyGlyIleArgSerAsnPro
1020 gtcacccctgaatgtcctctatggtccagacctccccagaatttacccttacttcacctat  1079
     ValThrLeuAsnValLeuTyrGlyProAspLeuProArgIleTyrProTyrPheThrTyr
1080 taccgttcaggagaaaacctcgacttgtcctgctttgcggactctaacccaccggcagag  1139
     TyrArgSerGlyGluAsnLeuAspLeuSerCysPheAlaAspSerAsnProProAlaGlu
1140 tatttttggacaattaatgggaagtttcagctatcaggacaaaagctctttatcccccaa  1199
     TyrPheTrpThrIleAsnGlyLysPheGlnLeuSerGlyGlnLysLeuPheIleProGln
1200 attactacaaatcatagcgggctctatgcttgctctgttcgtaactcagccactggcaag  1259
     IleThrThrAsnHisSerGlyLeuTyrAlaCysSerValArgAsnSerAlaThrGlyLys
1260 gaaatctccaaatccatgatagtcaaagtctctggtccctgccatggaaaccagacagag  1319
     GluIleSerLysSerMetIleValLysValSerGlyProCysHisGlyAsnGlnThrGlu
1320 tctcattaatggctgccacaatagagacactgagaaaaagaacaggttgataccttcatg  1379
     SerHisEnd
1380 aaaattcaagacaaagaagaaaaaggctcaatgttattggactaaataatcaaaaggataa  1439
1440 tgttttcataatttttattggaaaatgtgctgattcttggaatgttttattctccagatt  1499
1500 tatgaacttttttcttcagcaattggtaaagtatacttttgtaaacaaaaattgaaaca   1559
1560 tttgcttttgctctctatctgagtgcccccc                               1591
```

It will be appreciated that the instant specification and claims are set forth by way of illustration and not limitation and that various modifications and changes may be made without departing from the spirit and scope of the present invention.

---

What is claimed is:

1. An isolated DNA sequence encoding a carcinoembryonic antigen (CEA) family member polypeptide, said isolated DNA sequence hybridizing to a nucleic acid sequence selected from the group consisting of TM-2 (SEQ ID NO.: 1), TM-3 (SEQ ID NO.: 2), KGCEA-1 (SEQ ID NO.: 8) and KGCEA-2 (SEQ ID NO.: 9) under the following conditions:

(a) hybridization in 2× SSSPE, 5× Denhardt's solution and 100 µg of denatured salmon sperm DNA per ml at 68° C., followed by (b) washing in 0.2× SSC, 0.25% SDS at 68° C.;

and said CEA family member polypeptide binding an antibody generated by immunizing an animal with intact CEA; wherein the isolated DNA sequence is not cLV7.

2. A continuous fragment of the DNA sequence according to claim 1, said continuous fragment being at least a 50 mer, said continuous fragment encoding a continuous polypeptide fragment of said CEA family member polypeptide and said continuous polypeptide fragment binding an antibody specific to said CEA family member polypeptide.

3. A replicable recombinant cloning vehicle having an insert comprising a nucleic acid according to claim 1.

4. A cell that is transfected, infected or injected with a recombinant cloning vehicle, said cloning vehicle according to claim 3.

5. A cell that is transfected with free nucleic acid, said free nucleic acid being a DNA sequence of claim 1 or 2.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 3173 nucleotides
        (B) TYPE: nucleic acid
        (C) STRANDEDNESS: single
        (D) TOPOLOGY: linear (xi) SEQUENCE DESCRIPTION: SEQ ID NO: 1:

```
CAGCCGTGCT CGAAGCGTTC CTGGAGCCCA AGCTGTCCTC                                40

CACAGGTGAA GACAGGGCCA GCAGGAGACA CC ATG GGC                                78
                                   Met Gly

CAC CTC TCA GCC CCA CTT CAC AGA GTG CGT GTA CCC TGG                      117
His Leu Ser Ala Pro Leu His Arg Val Arg Val Pro Trp
         5                  10                  15

CAG GGG CTT CTG CTC ACA GCC TCA CTT CTA ACC TTC TGG                      156
Gln Gly Leu Leu Leu Thr Ala Ser Leu Leu Thr Phe Trp
                 20                  25

AAC CCG CCC ACC ACT GCC CAG CTC ACT ACT GAA TCC ATG                      195
Asn Pro Pro Thr Thr Ala Gln Leu Thr Thr Glu Ser Met
 30                  35                  40

CCA TTC AAT GTT GCA GAG GGG AAG GAG GTT CTT CTC CTT                      234
Pro Phe Asn Val Ala Glu Gly Lys Glu Val Leu Leu Leu
             45                  50

GTC CAC AAT CTG CCC CAG CAA CTT TTT GGC TAC AGC TGG                      273
Val His Asn Leu Pro Gln Gln Leu Phe Gly Tyr Ser Trp
 55                  60                  65

TAC AAA GGG GAA AGA GTG GAT GGC AAC CGT CAA ATT GTA                      312
Tyr Lys Gly Glu Arg Val Asp Gly Asn Arg Gln Ile Val
         70                  75                  80

GGA TAT GCA ATA GGA ACT CAA CAA GCT ACC CCA GGG CCC                      351
Gly Tyr Ala Ile Gly Thr Gln Gln Ala Thr Pro Gly Pro
                 85                  90

GCA AAC AGC GGT CGA GAG ACA ATA TAC CCC AAT GCA TCC                      390
Ala Asn Ser Gly Arg Glu Thr Ile Tyr Pro Asn Ala Ser
 95                 100                 105

CTG CTG ATC CAG AAC GTC ACC CAG AAT GAC ACA GAA TTC                      429
Leu Leu Ile Gln Asn Val Thr Gln Asn Asp Thr Gly Phe
            110                 115

TAC ACC CTA CAA GTC ATA AAG TCA GAT CTT GTG AAT GAA                      468
Tyr Thr Leu Gln Val Ile Lys Ser Asp Leu Val Asn Glu
120                 125                 130

GAA GCA ACT GGA CAG TTC CAT GTA TAC CCG GAG CTG CCC                      507
Glu Ala Thr Gly Gln Phe His Val Tyr Pro Glu Leu Pro
            135                 140                 145

AAG CCC TCC ATC TCC AGC AAC AAC TCC AAC CCT GTG GAG                      546
Lys Pro Ser Ile Ser Ser Asn Asn Ser Asn Pro Val Glu
                150                 155
```

```
GAC AAG GAT GCT GTG GCC TCC ACC TGT GAA CCT GAG ACT                585
Asp Lys Asp Ala Val Ala Ser Thr Cys Glu Pro Glu Thr
    160             165             170

CAG GAC ACA ACC TAC CTG TGG TGG ATA AAC AAT CAG AGC                624
Gln Asp Thr Thr Tyr Leu Trp Trp Ile Asn Asn Gln Ser
            175             180

CTC CCG GTC AGT CCC AGG CTG CAG CTG TCC AAT GGC AAC                663
Leu Pro Val Ser Pro Arg Leu Gln Leu Ser Asn Gly Asn
185             190             195

AGG ACC CTC ACT CTA CTC AGT GTC ACA AGG AAT GAC ACA                702
Arg Thr Leu Thr Leu Leu Ser Val Thr Arg Asn Asp Thr
        200             205             210

GGA CCC TAT GAG TGT GAA ATA CAG AAC CCA GTG AGT GCG                741
Gly Pro Tyr Glu Cys Glu Ile Gln Asn Pro Val Ser Ala
                215             220

AAC CTC AGT GAC CCA GTC ACC TTG AAT GTC ACC TAT GGC                780
Asn Arg Ser Asp Pro Val Thr Leu Asn Val Thr Tyr Gly
225             230             235

CCG GAC ACC CCC ACC ATT TCC CCT TCA GAC ACC TAT TAC                819
Pro Asp Thr Pro Thr Ile Ser Pro Ser Asp Thr Tyr Tyr
        240             245

CGT CCA GGG GCA AAC CTC AGC CTC TCC TGC TAT GCA GCC                858
Arg Pro Gly Ala Asn Leu Ser Leu Ser Cys Tyr Ala Ala
250             255             260

TCT AAC CCA CCT GCA CAG TAC TCC TGG CTT ATC AAT GGA                897
Ser Asn Pro Pro Ala Gln Tyr Ser Trp Leu Ile Asn Gly
            265             270             275

ACA TTC CAG CAA AGC ACA CAA GAG CTC TTT ATC CCT AAC                936
Thr Phe Gln Gln Ser Thr Gln Glu Leu Phe Ile Pro Asn
                280             285

ATC ACT GTG AAT AAT AGT GGA TCC TAT ACC TGG CAC GCC                975
Ile Thr Val Asn Asn Ser Gly Ser Tyr Thr Trp His Ala
        290             295             300

AAT AAC TCA GTC ACT GGC TGC AAC AGG ACC ACA GTC AAG                1014
Asn Asn Ser Val Thr Gly Cys Asn Arg Thr Thr Val Lys
                305             310

ACG ATC ATA GTC ACT GAT AAT GCT CTA CCA CAA GAA AAT                1053
Thr Ile Ile Val Thr Asp Asn Ala Leu Pro Gln Glu Asn
315             320             325

GGC CTC TCA CCT GGG GCC ATT GCT GGC ATT GTG ATT GGA                1092
Gly Leu Ser Pro Gly Ala Ile Ala Gly Ile Val Ile Gly
        330             335             340

GTA GTG GCC CTG GTT GCT CTG ATA GCA GTA GCC CTG GCA                1131
Val Val Ala Leu Val Ala Leu Ile Ala Val Ala Leu Ala
                345             350

TGT TTT CTG CAT TTC GGG AAG ACC GGC AGG GCA AGC GAC                1170
Cys Phe Leu His Phe Gly Lys Thr Gly Arg Ala Ser Asp
        355             360             365

CAG CGT GAT CTC ACA GAG CAC AAA CCC TCA GTC TCC AAC                1209
Gln Arg Asp Leu Thr Glu His Lys Pro Ser Val Ser Asn
            370             375

CAC ACT CAG GAC CAC TCC AAT GAC CCA CCT AAC AAG ATG                1248
His Thr Gln Asp His Ser Asn Asp Pro Pro Asn Lys Met
380             385             390

AAT GAA GTT ACT TAT TCT ACC CTG AAC TTT GAA GCC CAG                1287
Asn Glu Val Thr Tyr Ser Thr Leu Asn Phe Glu Ala Gln
        395             400             405

CAA CCC ACA CAA CCA ACT TCA GCC TCC CCA TCC CTA ACA                1326
Gln Pro Thr Gln Pro Thr Ser Ala Ser Pro Ser Leu Thr
            410             415
```

| | |
|---|---|
| GCC ACA GAA ATA ATT TAT TCA GAA GTA AAA AAG CAG<br>Ala Thr Glu Ile Ile Tyr Ser Glu Val Lys Lys Gln<br>   420                       425 | 1362 |
| TAATGAAACC TGTCCTGCTC ACTGCAGTGC TGATGTATTT | 1402 |
| CAAGTCTCTC ACCCTCATCA CTAGGAGATT CCTTTCCCCT | 1442 |
| GTAGGGTAGA GGGGTGGGGA CAGAAACAAC TTTCTCCTAC | 1482 |
| TCTTCCTTCC TAATAGGCAT CTCCAGGCTG CCTGGTCACT | 1522 |
| GCCCCTCTCT CAGTGTCAAT AGATGAAAGT ACATTGGGAG | 1562 |
| TCTGTAGGAA ACCCAACCTT CTTGTCATTG AAATTTGGCA | 1602 |
| AAGCTGACTT TGGGAAAGAG GGACCAGAAC TTCCCCTCCC | 1642 |
| TTCCCCTTTT CCCAACCTGG ACTTGTTTTA AACTTGCCTG | 1682 |
| TTCAGAGCAC TCATTCCTTC CCACCCCCAG TCCTGTCCTA | 1722 |
| TCACTCTAAT TCGATTTGC CATAGCCTTG AGGTTATGTC | 1762 |
| CTTTTCCATT AAGTACATGT GCCAGGAAAC AGCGAGAGAG | 1802 |
| AGAAAGTAAA CGGCAGTAAT GCTTCTCCTA TTTCTCCAAA | 1842 |
| GCCTTGTGTG AACTAGCAAA GAGAAGAAAA TCAAATATAT | 1882 |
| AACCAATAGT GAAATGCCAC AGGTTTGTCC ACTGTCAGGG | 1922 |
| TTGTCTACCT GTAGGATCAG GGTCTAAGCA CCTTGGTGCT | 1962 |
| TAGCTAGAAT ACCACCTAAT CCTTCTGGCA AGCCTGTCTT | 2002 |
| CAGAGAACCC ACTAGAAGCA ACTAGGAAAA ATCACTTGCC | 2042 |
| AAAATCCAAG GCAATTCCTG ATGGAAAATG CAAAAGCACA | 2082 |
| TATATGTTTT AATATCTTTA TGGGCTCTGT TCAAGGCAGT | 2122 |
| GCTGAGAGGG AGGGGTTATA GCTTCAGGAG GGAACCAGCT | 2162 |
| TCTGATAAAC ACAATCTGCT AGGAACTTGG GAAAGGAATC | 2202 |
| AGAGAGCTGC CCTTCAGCGA TTATTTAAAT TGTTAAAGAA | 2242 |
| TACACAATTT GGGGTATTGG GATTTTTCTC CTTTTCTCTG | 2282 |
| AGACATTCCA CCATTTTAAT TTTTGTAACT GCTTATTTAT | 2322 |
| GTGAAAAGGG TTATTTTTAC TTAGCTTAGC TATGTCAGCC | 2362 |
| AATCCGATTG CCTTAGGTGA AAGAAACCAC CGAAATCCCT | 2402 |
| CAGGTCCCTT GGTCAGGAGC CTCTCAAGAT TTTTTTTGTC | 2442 |
| AGAGGCTCCA AATAGAAAAT AAGAAAAGGT TTTCTTCATT | 2482 |
| CATGGCTAGA GCTAGATTTA ACTCAGTTTC TAGGCACCTC | 2522 |
| AGACCAATCA TCAACTACCA TTCTATTCCA TGTTTGCACC | 2562 |
| TGTGCATTTT CTGTTTGCCC CCATTCACTT TGTCAGGAAA | 2602 |
| CCTTGGCCTC TGCTAAGGTG TATTTGGTCC TTGAGAAGTG | 2642 |
| GGAGCACCCT ACAGGGACAC TATCACTCAT GCTGGTGGCA | 2682 |
| TTGTTTACAG CTAGAAAGCT GCACTGGTGC TAATGCCCCT | 2722 |
| TGGGAAATGG GGCTGTGAGG AGGAGGATTA TAACTTAGGC | 2762 |
| CTAGCCTCTT TTAACAGCCT CTGAAATTTA TCTTTTCTTC | 2802 |
| TATGGGGTCT ATAAATGTAT CTTATAATAA AAAGGAAGGA | 2842 |
| CAGGAGGAAG ACAGGCAAAT GTACTTCTCA CCCAGTCTTC | 2882 |

```
TACACAGATG GAATCTCTTT GGGGCTAAGA GAAAGGTTTT                                      2922

ATTCTATATT GCTTACCTGA TCTCATGTTA GGCCTAAGAG                                      2962

GCTTTCTCCA GGAGGATTAG CTTGGAGTTC TCTATACTCA                                      3002

GGTACCTCTT TCAGGGTTTT CTAACCCTGA CACGGACTGT                                      3042

GCATACTTTC CCTCATCCAT GCTGTGCTGT GTTATTTAAT                                      3082

TTTTCCTGGC TAAGATCATG TCTGAATTAT GTATGAAAAT                                      3122

TATTCTATGT TTTTATAATA AAATAATAT ATCAGACATC                                       3162

GAAAAAAAA A                                                                      3173

(2) INFORMATION FOR SEQ ID NO: 2:

(i) SEQUENCE CHARACTERISTICS:
        (A) LENGTH: 1630 nucleotides
        (B) TYPE:   nucleic acid
        (C) STRANDEDNESS: single
        (D) TOPOLOGY:  linear (xi) SEQUENCE DESCRIPTION: SEQ ID NO: 2:

CAGCCGTGCT CGAAGCGTTC CTGGAGCCCA AGCTCTCCTC                                      40

CACAGGTGAA GACAGGGCCA GCAGGAGACA                                                 70

CC ATG GGG CAC CTC TCA GCC CCA CTT CAC AGA GTG CGT                               108
   Met Gly His Leu Ser Ala Pro Leu His Arg Val Arg
                    5                  10

GTA CCC TGG CAG GGG CTT CTG CTC ACA GCC TCA CTT CTA                              147
Val Pro Trp Gln Gly Leu Leu Leu Thr Ala Ser Leu Leu
            15                  20                  25

ACC TTC TGG AAC CCG CCC ACC ACT GCC CAG CTC ACT ACT                              186
Thr Phe Trp Asn Pro Pro Thr Thr Ala Gln Leu Thr Thr
                30                  35

GAA TCC ATG CCA TTC AAT GTT GCA GAG GGG AAG GAG GTT                              225
Glu Ser Met Pro Phe Asn Val Ala Glu Gly Lys Glu Val
 40                  45                  50

CTT CTC CTT GTC CAC AAT CTG CCC CAG CAA CTT TTT GGC                              264
Leu Leu Leu Val His Asn Leu Pro Gln Gln Leu Phe Gly
                    55                  60

TAC AGC TGG TAC AAA GGG GAA AGA GTG GAT GGC AAC CGT                              303
Tyr Ser Trp Tyr Lys Gly Glu Arg Val Asp Gly Asn Arg
 65                  70                  75

CAA ATT GTA GGA TAT GCA ATA GGA ACT CAA CAA GCT ACC                              342
Gln Ile Val Gly Tyr Ala Ile Gly Thr Gln Gln Ala Thr
                80                  85                  90

CCA GGG CCC GCA AAC AGC GGT CGA GAG ACA ATA TAC CCC                              381
Pro Gly Pro Ala Asn Ser Gly Arg Glu Thr Ile Tyr Pro
                    95                  100

AAT GCA TCC CTG CTG ATC CAG AAC GTC ACC CAG AAT GAC                              420
Asn Ala Ser Leu Leu Ile Gln Asn Val Thr Gln Asn Asp
 105                 110                 115

ACA GGA TTC TAC ACC CTA CAA GTC ATA AAG TCA GAT CTT                              459
Thr Gly Phe Tyr Thr Leu Gln Val Ile Lys Ser Asp Leu
                120                 125

GTG AAT GAA GAA GCA ACT GGA CAG TTC CAT GTA TAC CCG                              498
Val Asn Glu Glu Ala Thr Gly Gln Phe His Val Tyr Pro
130                 135                 140

GAG CTG CCC AAG CCC TCC ATC TCC AGC AAC AAC TCC AAC                              537
Glu Leu Pro Lys Pro Ser Ile Ser Ser Asn Asn Ser Asn
                145                 150                 155
```

| | |
|---|---|
| CCT GTG GAG GAC AAG GAT GCT GTG GCC TTC ACC TGT GAA<br>Pro Val Glu Asp Lys Asp Ala Val Ala Phe Thr Cys Glu<br>160                            165 | 576 |
| CCT GAG ACT CAG GAC ACA ACC TAC CTG TGG TGG ATA AAC<br>Pro Glu Thr Gln Asp Thr Thr Tyr Leu Trp Trp Ile Asn<br>170                          175                     180 | 615 |
| AAT CAG AGC CTC CCG GTC AGT CCC AGG CTG CAG CTG TCC<br>Asn Gln Ser Leu Pro Val Ser Pro Arg Leu Gln Leu Ser<br>               185                     190 | 654 |
| AAT GGC AAC AGG ACC CTC ACT CTA CTC AGT GTC ACA AGG<br>Asn Gly Asn Arg Thr Leu Thr Leu Leu Ser Val Thr Arg<br>195                           200                     205 | 693 |
| AAT GAC ACA GGA CCC TAT GAG TGT GAA ATA CAG AAC CCA<br>Asn Asp Thr Gly Pro Tyr Glu Cys Glu Ile Gln Asn Pro<br>               210                     215                   220 | 732 |
| GTG AGT GCG AAC CGC AGT GAC CCA GTC ACC TTG AAT GTC<br>Val Ser Ala Asn Arg Ser Asp Pro Val Thr Leu Asn Val<br>225                           230 | 771 |
| AAC TAT GGC CCG GAC ACC CCC ACC ATT TCC CCT TCA GAC<br>Thr Tyr Gly Pro Asp Thr Pro Thr Ile Ser Pro Ser Asp<br>               235                     240                   245 | 810 |
| ACC TAT TAC CGT CCA GGG GCA AAC CTC AGC CTC TCC TGC<br>Thr Tyr Tyr Arg Pro Gly Ala Asn Leu Ser Leu Ser Cys<br>                 250                     255 | 849 |
| TAT GCA GCC TCT AAC CCA CCT GCA CAG TAC TCC TGG CTT<br>Tyr Ala Ala Ser Asn Pro Pro Ala Gln Tyr Ser Trp Leu<br>260                          265                     270 | 888 |
| ATC AAT GGA ACA TTC CAG CAA AGC ACA CAA GAG CTC TTT<br>Ile Asn Gly Thr Phe Gln Gln Ser Thr Gln Glu Leu Phe<br>               275                     280                   285 | 927 |
| ATC CCT AAC ATC ACT GTG AAT AAT AGT GGA TCC TAT ACC<br>Ile Pro Asn Ile Thr Val Asn Asn Ser Gly Ser Tyr Thr<br>                 290                     295 | 966 |
| TGC CAC GCC AAT AAC TCA GTC ACT GGC TGC AAC AGG ACC<br>Cys His Ala Asn Asn Ser Val Thr Gly Cys Asn Arg Thr<br>300                           305                     310 | 1005 |
| ACA GTC AAG ACG ATC ATA GTC ACT GAG CTA AGT CCA GTA<br>Thr Val Lys Thr Ile Ile Val Thr Glu Leu Ser Pro Val<br>               315                     320 | 1044 |
| GTA GCA AAG CCC CAA ATC AAA GCC AGC AAG ACC ACA GTC<br>Val Ala Lys Pro Gln Ile Lys Ala Ser Lys Thr Thr Val<br>325                           330                     335 | 1083 |
| ACA GGA GAT AAG GAC TCT GTG AAC CTG ACC TGC TCC ACA<br>Thr Gly Asp Lys Asp Ser Val Asn Leu Thr Cys Ser Thr<br>               340                     345                   350 | 1122 |
| AAT GAC ACT GGA ATC TCC ATC CGT TGG TTC TTC AAA AAC<br>Asn Asp Thr Gly Ile Ser Ile Arg Trp Phe Phe Lys Asn<br>                 355                     360 | 1161 |
| CAG AGT CTC CCG TCC TCG GAG AGG ATG AAG CTG TCC CAG<br>Gln Ser Leu Pro Ser Ser Glu Arg Met Lys Leu Ser Gln<br>365                           370                     375 | 1200 |
| GGC AAC ACC ACC CTC AGC ATA AAC CCT GTC AAG AGG GAG<br>Gly Asn Thr Thr Leu Ser Ile Asn Pro Val Lys Arg Glu<br>               380                     385 | 1239 |
| GAT GCT GGG ACG TAT TGG TGT GAG GTC TTC AAC CCA ATC<br>Asp Ala Gly Thr Tyr Trp Cys Glu Val Phe Asn Pro Ile<br>390                           395                     400 | 1278 |
| AGT AAG AAC CAA AGC GAC CCC ATC ATG CTG AAC GTA AAC<br>Ser Lys Asn Gln Ser Asp Pro Ile Met Leu Asn Val Asn<br>               405                     410                   415 | 1317 |

| | |
|---|---|
| TAT AAT GCT CTA CCA CAA GAA AAT GGC CTC TCA CCT GGG<br>Tyr Asn Ala Leu Pro Gln Glu Asn Gly Leu Ser Pro Gly<br>420                                425 | 1356 |
| GCC ATT GCT GGC ATT GTG ATT GGA GTA GTG GCC CTG GTT<br>Ala Ile Ala Gly Ile Val Ile Gly Val Val Ala Leu Val<br>430                    435                              440 | 1395 |
| GCT CTG ATA GCA GTA GCC CTG GCA TGT TTT CTG CAT TTC<br>Ala Leu Ile Ala Val Ala Leu Ala Cys Phe Leu His Phe<br>              445                              450 | 1434 |
| GGG AAG ACC GGC AGC TCA GGA CCA CTC CAA<br>Gly Lys Thr Gly Ser Ser Gly Pro Leu Gln<br>455                          460 | 1464 |
| TGACCCACCT AACAAGATGA ATGAAGTTAC TTATTCTACC | 1504 |
| CTGAACTTTG AAGCCCAGCA ACCCACACAA CCAACTTCAG | 1544 |
| CCTCCCCATC CCTAACAGCC ACAGAAATAA TTTATTCAGA | 1584 |
| AGTAAAAAAG CAGTAATGAA ACCTGAAAAA AAAAAAAAAA | 1624 |
| AAAAAA | 1630 |

(2) INFORMATION FOR SEQ ID NO: 3:

(i) SEQUENCE CHARACTERISTICS:
        (A) LENGTH: 1339 nucleotides
        (B) TYPE: nucleic acid
        (C) STRANDEDNESS: single
        (D) TOPOLOGY: linear (xi) SEQUENCE DESCRIPTION: SEQ ID NO: 3:

| | |
|---|---|
| CAGCCGTGCT CGAAGCGTTC CTGGAGCCCA AGCTCTCCTC | 40 |
| CACAGGTGAA GACAGGGCCA GCAGGAGACA CC ATG<br>                                                        Met | 75 |
| GGG CAC CTC TCA GCC CCA CTT CAC AGA GTG CGT GTA CCC<br>Gly His Leu Ser Ala Pro Leu His Arg Val Arg Val Pro<br>              5                              10 | 114 |
| TGG CAG GGG CTT CTG CTC ACA GCC TCA CTT CTA ACC TTC<br>Trp Gln Gly Leu Leu Leu Thr Ala Ser Leu Leu Thr Phe<br>15                    20                          25 | 153 |
| TGG AAC CCG CCC ACC ACT GCC CAG CTC ACT ACT GAA TCC<br>Trp Asn Pro Pro Thr Thr Ala Gln Leu Thr Thr Glu Ser<br>          30                    35                    40 | 192 |
| ATG CCA TTC AAT GTT GCA GAG GGG AAG GAG GTT CTT CTC<br>Met Pro Phe Asn Val Ala Glu Gly Lys Glu Val Leu Leu<br>                              45                      50 | 231 |
| CTT GTC CAC AAT CTG CCC CAG CAA CTT TTT GGC TAC AGC<br>Leu Val His Asn Leu Pro Gln Gln Leu Phe Gly Tyr Ser<br>55                          60                      65 | 270 |
| TGG TAC AAA GGG GAA AGA GTG GAT GGC AAC CGT CAA ATT<br>Trp Tyr Lys Gly Glu Arg Val Asp Gly Asn Arg Gln Ile<br>                      70                    75 | 309 |
| GTA GGA TAT GCA ATA GGA ACT CAA CAA GCT ACC CCA GGG<br>Val Gly Tyr Ala Ile Gly Thr Gln Gln Ala Thr Pro Gly<br>80                    85                              90 | 348 |
| CCC GCA AAC AGC GGT CGA GAG ACA ATA TAC CCC AAT GCA<br>Pro Ala Asn Ser Gly Arg Glu Thr Ile Tyr Pro Asn Ala<br>              95                          100                    105 | 387 |
| TCC CTG CTG ATC CAG AAC GTC ACC CAG AAT GAC ACA GGA<br>Ser Leu Leu Ile Gln Asn Val Thr Gln Asn Asp Thr Gly<br>                        110                      115 | 426 |

```
TTC TAC ACC CTA CAA GTC ATA AAG TCA GAT CTT GTG AAT                465
Phe Tyr Thr Leu Gln Val Ile Lys Ser Asp Leu Val Asn
    120                 125                 130

GAA GAA GCA ACT GGA CAG TTC CAT GTA TAC CCG GAG CTG                504
Glu Glu Ala Thr Gly Gln Phe His Val Tyr Pro Glu Leu
            135                 140

CCC AAG CCC TCC ATC TCC AGC AAC AAC TCC AAC CCT GTG                543
Pro Lys Pro Ser Ile Ser Ser Asn Asn Ser Asn Pro Val
145                 150                 155

GAG GAC AAG GAT GCT GTG GCC TTC ACC TGT GAA CCT GAG                582
Glu Asp Lys Asp Ala Val Ala Phe Thr Cys Glu Pro Glu
                160                 165                 170

ACT CAG GAC ACA ACC TAC CTG TGG TGG ATA AAC AAT CAG                621
Thr Gln Asp Thr Thr Tyr Leu Trp Trp Ile Asn Asn Gln
                    175                 180

AGC CTC CCG GTC AGT CCC AGG CTG CAG CTG TCC AAT GGC                660
Ser Leu Pro Val Ser Pro Arg Leu Gln Leu Ser Asn Gly
        185                 190                 195

AAC AGG ACC CTC ACT CTA CTC AGT GTC ACA AGG AAT GAC                699
Asn Arg Thr Leu Thr Leu Leu Ser Val Thr Arg Asn Asp
            200                 205

ACA GGA CCC TAT GAG TGT GAA ATA CAG AAC CCA GTG AGT                738
Thr Gly Pro Tyr Glu Cys Glu Ile Gln Asn Pro Val Ser
210                 215                 220

GCG AAC CGC AGT GAC CCA GTC ACC TTG AAT GTC ACC TAT                777
Ala Asn Arg Ser Asp Pro Val Thr Leu Asn Val Thr Tyr
                225                 230                 235

GGC CCG GAC ACC CCC ACC ATT TCC CCT TCA GAC ACC TAT                816
Gly Pro Asp Thr Pro Thr Ile Ser Pro Ser Asp Thr Tyr
                    240                 245

TAC CGT CCA GGG GCA AAC CTC AGC CTC TCC TGC TAT GCA                855
Tyr Arg Pro Gly Ala Asn Leu Ser Leu Ser Cys Tyr Ala
        250                 255                 260

GCC TCT AAC CCA CCT GCA CAG TAC TCC TGG CTT ATC AAT                894
Ala Ser Asn Pro Pro Ala Gln Tyr Ser Trp Leu Ile Asn
            265                 270

GGA ACA TTC CAG CAA AGC ACA CAA GAG CTC TTT ATC CCT                933
Gly Thr Phe Gln Gln Ser Thr Gln Glu Leu Phe Ile Pro
275                 280                 285

AAC ATC ACT GTG AAT AAT AGT GGA TCC TAT ACC TGC CAC                972
Asn Ile Thr Val Asn Asn Ser Gly Ser Tyr Thr Cys His
                290                 295                 300

GCC AAT AAC TCA GTC ACT GGC TGC AAC AGG ACC ACA GTC                1011
Ala Asn Asn Ser Val Thr Gly Cys Asn Arg Thr Thr Val
                    305                 310

AAG ACG ATC ATA GTC ACT GAT AAT GCT CTA CCA CAA GAA                1050
Lys Thr Ile Ile Val Thr Asp Asn Ala Leu Pro Gln Glu
315                 320                 325

AAT GGC CTC TCA CCT GGG GCC ATT GCT GGC ATT GTG ATT                1089
Asn Gly Leu Ser Pro Gly Ala Ile Ala Gly Ile Val Ile
                330                 335

GGA GTA GTG GCC CTG GTT GCT CTG ATA GCA GTA GCC CTG                1128
Gly Val Val Ala Leu Val Ala Leu Ile Ala Val Ala Leu
340                 345                 350

GCA TGT TTT CTG CAT TTC GGG AAG ACC GGC AGC TCA GGA                1167
Ala Cys Phe Leu His Phe Gly Lys Thr Gly Ser Ser Gly
                355                 360                 365

CCA CTC CAA TGACCCACCT AACAAGATGA ATGAAGTTAC                        1206
Pro Leu Gln
```

```
TTATTCTACC CTGAACTTTG AAGCCCAGCA ACCCACACAA                    1246

CCAACTTCAG CCTCCCCATC CCTAACAGCC ACAGAAATAA                    1286

TTTATTCAGA AGTAAAAAAG CAGTAATGAA ACCTGAAAAA                    1326

AAAAAAAAAA AAA                                                 1339
```

(2) INFORMATION FOR SEQ ID NO: 4:

(i) SEQUENCE CHARACTERISTICS:
        (A) LENGTH: 862 nucleotides
        (B) TYPE: nucleic acid
        (C) STRANDEDNESS: single
        (D) TOPOLOGY: linear (xi) SEQUENCE DESCRIPTION: SEQ ID NO: 4:

```
GGGGTTTACA CAACCACCAC CCCATCAAAC CCTTCATCAC                     40

CAGCAACAAC TCCAACCCCG TGGAGGATGA GGATGCTGTA                     80

GCCTTAACCT GTGAACCTCA GATTCAGAAC ACAACCTACC                    120

TGTGGTGGGT AAATAATCAG AGCCTCCCGG TCAGTCCCAG                    160

GCTGCAGCTG TCCAATGACA ACAGGACCCT CACTCTACTC                    200

AGTGTCACAA GGAATGATGT AGGACCCTAT GAGTGTGGAA                    240

TCCAGAACGA ATTAAGTGTT GACCACAGCG ACCCAGTCAT                    280

CCTGAATGTC CTCTATGGCC CAGACGACCC CACCATTTCC                    320

CCCTCATACA CCTATTACCG TCCAGGGGTG AACCTCAGCC                    360

TCTCCTGCCA TGCAGCCTCT AACCCACCTG CACAGTATTC                    400

TTGGCTGATT GATGGGAACA TCCAGCAACA CACACAAGAG                    440

CTCTTTATCT CCAACATCAC TGAGAAGAAC AGCGGACTCT                    480

ATACCTGCCA GGCCAATAAC TCAGCCAGTG GCCACAGCAG                    520

GACTACAGTC AAGACAATCA CAGTCTCTGC GGACGTGCCC                    560

AAGCCCTCCA TCTCCAGCAA CAACTCCAAA CCCGTGGAGG                    600

ACAAGGATGC TGTGGCCTTC CACTGTGAAC CTGAGGCTCA                    640

GAACACAACC TACCTGTGGT GGGTAAATGG TCAGAGCCTC                    680

CCAGTCAGTC CCAGGCTGCA GCTGTCCAAT GGCAACAGGA                    720

CCCTCACTCT ATTCAATGTC ACAAGAAATG ACGCAAGAGC                    760

CTATGTATGT GGAATCCAGA ACTCAGTGAG TGCAAACCGC                    800

AGTGACCCAG TCACCCTGGA TGTCCTCTAT GGGCCGGACA                    840

CCCCCATCAT TTCCCCCCCC CC                                       862
```

(2) INFORMATION FOR SEQ ID NO: 5:

(i) SEQUENCE CHARACTERISTICS:
        (A) LENGTH: 2839 nucleotides
        (B) TYPE: nucleic acid
        (C) STRANDEDNESS: single
        (D) TOPOLOGY: linear (xi) SEQUENCE DESCRIPTION: SEQ ID NO: 5:

```
CACC ATG GAG TCT CCC TCG GCC CCT CTC CAC AGA TGG TGC           40
     Met Glu Ser Pro Ser Ala Pro Leu His Arg Trp Cys
          -30                     -25
```

| | |
|---|---|
| ATC CCC TGG CAG AGG CTC CTG CTC ACA GCC TCA CTT CTA<br>Ile Pro Trp Gln Arg Leu Leu Leu Thr Ala Ser Leu Leu<br>     -20                        -15                     -10 | 79 |
| ACC TTC TGG AAC CCG CCC ACC ACT GCC AAG CTC ACT ATT<br>Thr Phe Trp Asn Pro Pro Thr Thr Ala Lys Leu Thr Ile<br>               -5                         1 | 118 |
| GAA TCC ACG CCG TTC AAT GTC GCA GAG GGG AAG GAG GTG<br>Glu Ser Thr Pro Phe Asn Val Ala Glu Gly Lys Glu Val<br>5                        10                    15 | 157 |
| CTT CTA CTT GTC CAC AAT CTG CCC CAG CAT CTT TTT GGC<br>Leu Leu Leu Val His Asn Leu Pro Gln His Leu Phe Gly<br>        20                      25                    30 | 196 |
| TAC AGC TGG TAC AAA GGT GAA AGA GTG GAT GGC AAC CGT<br>Tyr Ser Trp Tyr Lys Gly Glu Arg Val Asp Gly Asn Arg<br>            35                      40 | 235 |
| CAA ATT ATA GGA TAT GTA ATA GGA ACT CAA CAA GCT ACC<br>Gln Ile Ile Gly Tyr Val Ile Gly Thr Gln Gln Ala Thr<br>    45                     50                     55 | 274 |
| CCA GGG CCC GCA TAC AGT GGT CGA GAG ATA ATA TAC CCC<br>Pro Gly Pro Ala Tyr Ser Gly Arg Glu Ile Ile Tyr Pro<br>         60                      65 | 313 |
| AAT GCA TCC CTG CTG ATC CAG AAC ATC ATC CAG AAT GAC<br>Asn Ala Ser Leu Leu Ile Gln Asn Ile Ile Gln Asn Asp<br>70                      75                    80 | 352 |
| ACA GGA TTC TAC ACC CTA CAC GTC ATA AAG TCA GAT CTT<br>Thr Gly Phe Tyr Thr Leu His Val Ile Lys Ser Asp Leu<br>         85                      90                 95 | 391 |
| GTG AAT GAA GAA GCA ACT GGC CAG TTC CGG GTA TAC CCG<br>Val Asn Glu Glu Ala Thr Gly Gln Phe Arg Val Tyr Pro<br>                100                    105 | 430 |
| GAG CTG CCC AAG CCC TCC ATC TCC AGC AAC AAC TCC AAA<br>Glu Leu Pro Lys Pro Ser Ile Ser Ser Asn Asn Ser Lys<br>110                   115                    120 | 469 |
| CCC GTG GAG GAC AAG GAT GCT GTG GCC TTC ACC TGT GAA<br>Pro Val Glu Asp Lys Asp Ala Val Ala Phe Thr Cys Glu<br>                125                    130 | 508 |
| CCT GAG ACT CAG GAC GCA ACC TAC CTG TGG TGG GTA AAC<br>Pro Glu Thr Gln Asp Ala Thr Tyr Leu Trp Trp Val Asn<br>135                   140                    145 | 547 |
| AAT CAG AGC CTC CCG GTC AGT CCC AGG CTG CAG CTG TCC<br>Asn Gln Ser Leu Pro Val Ser Pro Arg Leu Gln Leu Ser<br>            150                  155                160 | 586 |
| AAT GGC AAC AGG ACC CTC ACT CTA TTC AAT GTC ACA AGA<br>Asn Gly Asn Arg Thr Leu Thr Leu Phe Asn Val Thr Arg<br>                165                    170 | 625 |
| AAT GAA CAA GCA AGC TAC AAA TGT GAA ACC CAG AAC CCA<br>Asn Glu Gln Ala Ser Tyr Lys Cys Glu Thr Gln Asn Pro<br>175                   180                    185 | 664 |
| GTG AGT GCC AGG CGC AGT GAT TCA GTC ATC CTG AAT GTC<br>Val Ser Ala Arg Arg Ser Asp Ser Val Ile Leu Asn Val<br>            190                  195 | 703 |
| CTC TAT GGC CCG GAT GCC CCC ACC ATT TCC CCT CTA AAC<br>Leu Tyr Gly Pro Asp Ala Pro Thr Ile Ser Pro Leu Asn<br>200                   205                    210 | 742 |
| ACA TCT TAC AGA TCA GGG GAA AAT CTG AAC CTC TCC TGC<br>Thr Ser Tyr Arg Ser Gly Glu Asn Leu Asn Leu Ser Cys<br>            215                  220                225 | 781 |
| CAC GCA GCC TCT AAC CCA CCT GCA CAG TAC TCT TGG TTT<br>His Ala Ala Ser Asn Pro Pro Ala Gln Tyr Ser Trp Phe<br>                230                    235 | 820 |

| | |
|---|---|
| GTC AAT GGG ACT TTC CAG CAA TCC ACC CAA GAG CTC TTT<br>Val Asn Gly Thr Phe Gln Gln Ser Thr Gln Glu Leu Phe<br>240                        245                        250 | 859 |
| ATC CCC AAC ATC ACT GTG AAT AAT AGT GGA TCC TAT ACG<br>Ile Pro Asn Ile Thr Val Asn Asn Ser Gly Ser Tyr Thr<br>              255                        260 | 898 |
| TGC CAA GCC CAT AAC TCA GAC ACT GGC CTC AAT AGG ACC<br>Cys Gln Ala His Asn Ser Asp Thr Gly Leu Asn Arg Thr<br>265                        270                        275 | 937 |
| ACA GTC ACG ACG ATC ACA GTC TAT GCA GAG CCA CCC AAA<br>Thr Val Thr Thr Ile Thr Val Tyr Ala Glu Pro Pro Lys<br>        280                        285                        290 | 976 |
| CCC TTC ATC ACC AGC AAC AAC TCC AAC CCC GTG GAG GAT<br>Pro Phe Ile Thr Ser Asn Asn Ser Asn Pro Val Glu Asp<br>              295                        300 | 1015 |
| GAG GAT GCT GTA GCC TTA ACC TGT GAA CCT GAG ATT CAG<br>Glu Asp Ala Val Ala Leu Thr Cys Glu Pro Glu Ile Gln<br>305                        310                        315 | 1054 |
| AAC ACA ACC TAC CTG TGG TGG GTA AAT AAT CAG AGC CTC<br>Asn Thr Thr Tyr Leu Trp Trp Val Asn Asn Gln Ser Leu<br>        320                        325 | 1093 |
| CCG GTC AGT CCC AGG CTG CAG CTG TCC AAT GAC AAC AGG<br>Pro Val Ser Pro Arg Leu Gln Leu Ser Asn Asp Asn Arg<br>330                        335                        340 | 1132 |
| ACC CTC ACT CTA CTC AGT GTC ACA AGG AAT GAT GTA GGA<br>Thr Leu Thr Leu Leu Ser Val Thr Arg Asn Asp Val Gly<br>              345                        350                        355 | 1171 |
| CCC TAT GAG TGT GGA ATC CAG AAC GAA TTA AGT GTT GAC<br>Pro Tyr Glu Cys Gly Ile Gln Asn Glu Leu Ser Val Asp<br>                      360                        365 | 1210 |
| CAC AGC GAC CCA GTC ATC CTG AAT GTC CTC TAT GGC CCA<br>His Ser Asp Pro Val Ile Leu Asn Val Leu Tyr Gly Pro<br>370                        375                        380 | 1249 |
| GAC GAC CCC ACC ATT TCC CCC TCA TAC ACC TAT TAC CGT<br>Asp Asp Pro Thr Ile Ser Pro Ser Tyr Thr Tyr Tyr Arg<br>              385                        390 | 1288 |
| CCA GGG GTG AAC CTC AGC CTC TCC TGC CAT GCA GCC TCT<br>Pro Gly Val Asn Leu Ser Leu Ser Cys His Ala Ala Ser<br>395                        400                        405 | 1327 |
| AAC CCA CCT GCA CAG TAT TCT TGG CTG ATT GAT GGG AAC<br>Asn Pro Pro Ala Gln Tyr Ser Trp Leu Ile Asp Gly Asn<br>              410                        415                        420 | 1366 |
| ATC CAG CAA CAC ACA CAA GAG CTC TTT ATC TCC ACC ATC<br>Ile Gln Gln His Thr Gln Glu Leu Phe Ile Ser Asn Ile<br>                      425                        430 | 1405 |
| ACT GAG AAG AAC AGC GGA CTC TAT ACC TGC CAG GCC AAT<br>Thr Glu Lys Asn Ser Gly Leu Tyr Thr Cys Gln Ala Asn<br>435                        440                        445 | 1444 |
| AAC TCA GCC AGT GGC CAC AGC AGG ACT ACA GTC AAG ACA<br>Asn Ser Ala Ser Gly His Ser Arg Thr Thr Val Lys Thr<br>              450                        455 | 1483 |
| ATC ACA GTC TCT GCG GAC GTG CCC AAG CCC TCC ATC TCC<br>Ile Thr Val Ser Ala Asp Val Pro Lys Pro Ser Ile Ser<br>460                        465                        470 | 1522 |
| AGC AAC AAC TCC AAA CCC GTG GAG GAC AAG GAT GCT GTG<br>Ser Asn Asn Ser Lys Pro Val Glu Asp Lys Asp Ala Val<br>              475                        480                        485 | 1561 |
| GCC TTC ACC TGT GAA CCT GAG GCT CAG AAC ACA ACC TAC<br>Ala Phe Thr Cys Glu Pro Glu Ala Gln Asn Thr Thr Tyr<br>                      490                        495 | 1600 |

```
CTG TGG TGG GTA AAT GGT CAG AGC CTC CCA GTC AGT CCC                    1639
Leu Trp Trp Val Asn Gly Gln Ser Leu Pro Val Ser Pro
    500                 505                 510

AGG CTG CAG CTG TCC AAT GGC AAC AGG ACC CTC ACT CTA                    1678
Arg Leu Gln Leu Ser Asn Gly Asn Arg Thr Leu Thr Leu
            515                 520

TTC AAT GTC ACA AGA AAT GAC GCA AGA GCC TAT GTA TGT                    1717
Phe Asn Val Thr Arg Asn Asp Ala Arg Ala Tyr Val Cys
525                 530                 535

GGA ATC CAG AAC TCA GTG AGT GCA AAC CGC AGT GAC CCA                    1756
Gly Ile Gln Asn Ser Val Ser Ala Asn Arg Ser Asp Pro
        540                 545                 550

GTC ACC CTG GAT GTC CTC TAT GGG CCG GAC ACC CCC ATC                    1795
Val Thr Leu Asp Val Leu Tyr Gly Pro Asp Thr Pro Ile
                555                 560

ATT TCC CCC CCA GAC TCG TCT TAC CTT TCG GGA GCG AAC                    1834
Ile Ser Pro Pro Asp Ser Ser Tyr Leu Ser Gly Ala Asn
565                 570                 575

CTC AAC CTC TCC TGC CAC TCG GCC TCT AAC CCA TCC CCG                    1873
Leu Asn Leu Ser Cys His Ser Ala Ser Asn Pro Ser Pro
            580                 585

CAG TAT TCT TGG CGT ATC AAT GGG ATA CCG CAG CAA CAC                    1912
Gln Tyr Ser Trp Arg Ile Asn Gly Ile Pro Gln Gln His
590                 595                 600

ACA CAA GTT CTC TTT ATC GCC AAA ATC ACG CCA AAT AAT                    1951
Thr Gln Val Leu Phe Ile Ala Lys Ile Thr Pro Asn Asn
        605                 610                 615

AAC GGG ACC TAT GCC TGT TTT GTC TCT AAC TTG GCT ACT                    1990
Asn Gly Thr Tyr Ala Cys Phe Val Ser Asn Leu Ala Thr
                620                 625

GGC CGC AAT AAT TCC ATA GTC AAG AGC ATC ACA GTC TCT                    2029
Gly Arg Asn Asn Ser Ile Val Lys Ser Ile Thr Val Ser
630                 635                 640

GCA TCT GGA ACT TCT CCT GGT CTC TCA GCT GGG GCC ACT                    2068
Ala Ser Gly Thr Ser Pro Gly Leu Ser Ala Gly Ala Thr
            645                 650

GTC GGC ATC ATG ATT GGA GTG CTG GTT GGG GTT GCT CTG                    2107
Val Gly Ile Met Ile Gly Val Leu Val Gly Val Ala Leu
655                 660                 665

ATA TAGCAGCCCT GGTGTAGTTT CTTCATTTCA GGAAGACTGA                        2150
Ile

CAGTTGTTTT GCTTCTTCCT TAAAGCATTT GCAACAGCTA                            2190

CAGTCTAAAA TTGCTTCTTT ACCAAGGATA TTTACAGAAA                            2230

ATACTCTGAC CAGAGATCGA GACCATCCTA GCCAACATCG                            2270

TGAAACCCCA TCTCTACTAA AAATACAAAA ATGAGCTGGG                            2310

CTTGGTGGCG CGCACCTGTA GTCCCAGTTA CTCGGGAGGC                            2350

TGAGGCAGGA GAATCGCTTG AACCCGGGAG GTGGAGATTG                            2390

CAGTGAGCCC AGATCGCACC ACTGCACTCC AGTCTGGCAA                            2430

CAGAGCAAGA CTCCATCTCA AAAGAAAAG AAAAGAAGAC                             2470

TCTGACCTGT ACTCTTGAAT ACAAGTTTCT GATACCACTG                            2510

CACTGTCTGA GAATTTCCAA AACTTTAATG AACTAACTGA                            2550

CAGCTTCATG AAACTGTCCA CCAAGATCAA GCAGAGAAAA                            2590

TAATTAATTT CATGGGGACT AAATGAACTA ATGAGGATAA                            2630
```

-continued

| | |
|---|---|
| TATTTTCATA ATTTTTTATT TGAAATTTTG CTGATTCTTT | 2670 |
| AAATGTCTTG TTTCCCAGAT TTCAGGAAAC TTTTTTTCTT | 2710 |
| TTAAGCTATC CACTCTTACA GCAATTTGAT AAAATATACT | 2750 |
| TTTGTGAACA AAAATTGAGA CATTTACATT TTATCCCTAT | 2790 |
| GTGGTCGCTC CAGACTTGGG AAACTATTCA TGAATATTTA | 2830 |
| TATTGTATG | 2839 |

(2) INFORMATION FOR SEQ ID NO: 6:

(i) SEQUENCE CHARACTERISTICS:
        (A) LENGTH: 3461 nucleotides
        (B) TYPE: nucleic acid
        (C) STRANDEDNESS: single
        (D) TOPOLOGY: linear (xi) SEQUENCE DESCRIPTION: SEQ ID NO: 6:

| | |
|---|---|
| CAGCCGTGCT CGAAGCGTTC CTGGAGCCCA AGCTCTCCTC | 40 |
| CACAGGTGAA GACAGGGCCA GCAGGAGACA CC ATG GGG<br>                                               Met Gly | 78 |
| CAC CTC TCA GCC CCA CTT CAC AGA GTC CGT GTA CCC TGG<br>His Leu Ser Ala Pro Leu His Arg Val Arg Val Pro Trp<br>         5                  10                  15 | 117 |
| CAG GGG CTT CTG CTC ACA GCC TCA CTT CTA ACC TTC TGG<br>Gln Gly Leu Leu Leu Thr Ala Ser Leu Leu Thr Phe Trp<br>                20                     25 | 156 |
| AAC CCG CCC ACC ACT GCC CAG CTC ACT ACT GAA TCC ATG<br>Asn Pro Pro Thr Thr Ala Gln Leu Thr Thr Glu Ser Met<br>     30                     35                       40 | 195 |
| CCA TTC AAT GTT GCA GAG GGG AAG GAG GTT CTT CTC CTT<br>Pro Phe Asn Val Ala Glu Gly Lys Glu Val Leu Leu Leu<br>                45                     50 | 234 |
| GTC CAC AAT CTG CCC CAG CAA CTT TTT GGC TAC AGC TGG<br>Val His Asn Leu Pro Gln Gln Leu Phe Gly Tyr Ser Trp<br> 55                    60                     65 | 273 |
| TAC AAA GGG GAA AGA GTG GAT GGC AAC CGT CAA ATT GTA<br>Tyr Lys Gly Glu Arg Val Asp Gly Asn Arg Gln Ile Val<br>         70                     75                       80 | 312 |
| GGA TAT GCA ATA GGA ACT CAA CAA GCT ACC CCA GGG CCC<br>Gly Tyr Ala Ile Gly Thr Gln Gln Ala Thr Pro Gly Pro<br>                85                              90 | 351 |
| GCA AAC AGC GGT CGA GAG ACA ATA TAC CCC AAT GCA TCC<br>Ala Asn Ser Gly Arg Glu Thr Ile Tyr Pro Asn Ala Ser<br>     95                     100                   105 | 390 |
| CTG CTG ATC CAG AAC GTC ACC CAG AAT GAC ACA GGA TTC<br>Leu Leu Ile Gln Asn Val Thr Gln Asn Asp Thr Gly Phe<br>         110                    115 | 429 |
| TAC ACC CTA CAA GTC ATA AAG TCA GAT CTT GTG AAT GAA<br>Tyr Thr Leu Gln Val Ile Lys Ser Asp Leu Val Asn Glu<br>120                   125                     130 | 468 |
| GAA GCA ACT GGA CAG TTC CAT GTA TAC CCG GAG CTG CCC<br>Glu Ala Thr Gly Gln Phe His Val Tyr Pro Glu Leu Pro<br>     135                    140                   145 | 507 |
| AAG CCC TCC ATC TCC AGC AAC AAC TCC ACC CCT GTG GAG<br>Lys Pro Ser Ile Ser Ser Asn Asn Ser Thr Pro Val Glu<br>                150                     155 | 546 |
| GAC AAG GAT GCT GTG GCC TTC ACC TGT GAA CCT GAG ACT<br>Asp Lys Asp Ala Val Ala Phe Thr Cys Glu Pro Glu Thr<br> 160                   165                     170 | 585 |

| | | |
|---|---|---|
| CAG GAC ACA ACC TAC CTG TGG TGG ATA AAC AAT CAG AGC<br>Gln Asp Thr Thr Tyr Leu Trp Trp Ile Asn Asn Gln Ser<br>               175                             180 | | 624 |
| CTC CCG GTC AGT CCC AGG CTG CAG CTG TCC AAT GGC AAC<br>Leu Pro Val Ser Pro Arg Leu Gln Leu Ser Asn Gly Asn<br>185                      190                      195 | | 663 |
| AGG ACC CTC ACT CTA CTC AGT GTC ACA AGG AAT GAC ACA<br>Arg Thr Leu Thr Leu Leu Ser Val Thr Arg Asn Asp Thr<br>            200                      205                    210 | | 702 |
| GGA CCC TAT GAG TGT GAA ATA CAG AAC CCA GTG AGT GCG<br>Gly Pro Tyr Glu Cys Glu Ile Gln Asn Pro Val Ser Ala<br>               215                            220 | | 741 |
| AAC CGC AGT GAC CCA GTC ACC TTG AAT GTC ACC TAT GGC<br>Asn Arg Ser Asp Pro Val Thr Leu Asn Val Thr Tyr Gly<br>225                      230                      235 | | 780 |
| CCG GAC ACC CCC ACC ATT TCC CCT TCA GAC ACC TAT TAC<br>Pro Asp Thr Pro Thr Ile Ser Pro Ser Asp Thr Tyr Tyr<br>            240                      245 | | 819 |
| CGT CCA GGG GCA AAC CTC AGC CTC TCC TGC TAT GCA GCC<br>Arg Pro Gly Ala Asn Leu Ser Leu Ser Cys Tyr Ala Ala<br>250                      255                      260 | | 858 |
| TCT AAC CCA CCT GCA CAG TAC TCC TGG CTT ATC AAT GGA<br>Ser Asn Pro Pro Ala Gln Tyr Ser Trp Leu Ile Asn Gly<br>               265                           270                    275 | | 897 |
| ACA TTC CAG CAA AGC ACA CAA GAG CTC TTT ATC CCT AAC<br>Thr Phe Gln Gln Ser Thr Gln Glu Leu Phe Ile Pro Asn<br>                      280                            285 | | 936 |
| ATC ACT GTG AAT AAT AGT GGA TCC TAT ACC TGC CAC GCC<br>Ile Thr Val Asn Asn Ser Gly Ser Tyr Thr Cys His Ala<br>            290                      295                    300 | | 975 |
| AAT AAC TCA GTC ACT GGC TGC AAC AGG ACC ACA GTC AAG<br>Asn Asn Ser Val Thr Gly Cys Asn Arg Thr Thr Val Lys<br>               305                            310 | | 1014 |
| ACG ATC ATA GTC ACT GAG CTA AGT CCA GTA GTA GCA AAG<br>Thr Ile Ile Val Thr Glu Leu Ser Pro Val Val Ala Lys<br>315                      320                      325 | | 1053 |
| CCC CAA ATC AAA GCC AGC AAG ACC ACA GTC ACA GGA GAT<br>Pro Gln Ile Lys Ala Ser Lys Thr Thr Val Thr Gly Asp<br>               330                            335                    340 | | 1092 |
| AAG GAC TCT GTG AAC CTG ACC TGC TCC ACA AAT GAC ACT<br>Lys Asp Ser Val Asn Leu Thr Cys Ser Thr Asn Asp Thr<br>                      345                            350 | | 1131 |
| GGA ATC TCC ATC CGT TGG TTC TTC AAA AAC CAG AGT CTC<br>Gly Ile Ser Ile Arg Trp Phe Phe Lys Asn Gln Ser Leu<br>355                      360                      365 | | 1170 |
| CCG TCC TCG GAG AGG ATG AAG CTG TCC CAG GGC AAC ACC<br>Pro Ser Ser Glu Arg Met Lys Leu Ser Gln Gly Asn Thr<br>               370                            375 | | 1209 |
| ACC CTC AGC ATA AAC CCT GTC AAG AGG GAG GAT GCT GGG<br>Thr Leu Ser Ile Asn Pro Val Lys Arg Glu Asp Ala Gly<br>380                      385                      390 | | 1248 |
| ACG TAT TGG TGT GAG GTC TTC AAC CCA ATC AGT AAG AAC<br>Thr Tyr Trp Cys Glu Val Phe Asn Pro Ile Ser Lys Asn<br>               395                           400                    405 | | 1287 |
| CAA AGC GAC CCC ATC ATG CTG AAC GTA AAC TAT AAT GCT<br>Gln Ser Asp Pro Ile Met Leu Asn Val Asn Tyr Asn Ala<br>            410                      415 | | 1326 |
| CTA CCA CAA GAA AAT GGC CTC TCA CCT GGG GCC ATT GCT<br>Leu Pro Gln Glu Asn Gly Leu Ser Pro Gly Ala Ile Ala<br>420                      425                      430 | | 1365 |

| | |
|---|---|
| GGC ATT GTG ATT GGA GTA GTG GCC CTG GTT GCT CTG ATA<br>Gly Ile Val Ile Gly Val Val Ala Leu Val Ala Leu Ile<br>                 435                              440 | 1404 |
| GCA GTA GCC CTG GCA TGT TTT CTG CAT TTC GGG AAG ACC<br>Ala Val Ala Leu Ala Cys Phe Leu His Phe Gly Lys Thr<br>445                        450                        455 | 1443 |
| GGC AGG GCA AGC GAC CAG CGT GAT CTC ACA GAG CAC AAA<br>Gly Arg Ala Ser Asp Gln Arg Asp Leu Thr Glu His Lys<br>                 460                        465                       470 | 1482 |
| CCC TCA GTC TCC AAC CAC ACT CAG GAC CAC TCC AAT GAC<br>Pro Ser Val Ser Asn His Thr Gln Asp His Ser Asn Asp<br>                         475                             480 | 1521 |
| CCA CCT AAC AAG ATG AAT GAA GTT ACT TAT TCT ACC CTG<br>Pro Pro Asn Lys Met Asn Glu Val Thr Tyr Ser Thr Leu<br>485                        490                        495 | 1560 |
| AAC TTT GAA GCC CAG CAA CCC ACA CAA CCA ACT TCA GCC<br>Asn Phe Glu Ala Gln Gln Pro Thr Gln Pro Thr Ser Ala<br>                 500                        505 | 1599 |
| TCC CCA TCC CTA ACA GCC ACA GAA ATA ATT TAT TCA GAA<br>Ser Pro Ser Leu Thr Ala Thr Glu Ile Ile Tyr Ser Glu<br>510                        515                        520 | 1638 |
| GTA AAA AAG CAG TAATGAAACC TGTCCTGCTC ACTGCAGTGC<br>Val Lys Lys Gln<br>            525 | 1680 |
| TGATGTATTT CAAGTCTCTC ACCCTCATCA CTAGGAGATT | 1720 |
| CCTTTCCCCT GTAGGGTAGA GGGGTGGGGA CAGAAACAAC | 1760 |
| TTTCTCCTAC TCTTCCTTCC TAATAGGCAT CTCCAGGCTG | 1800 |
| CCTGGTCACT GCCCCTCTCT CAGTGTCAAT AGATGAAAGT | 1840 |
| ACATTGGGAG TCTGTAGGAA ACCCAACCTT CTTGTCATTG | 1880 |
| AAATTTGGCA AAGCTGACTT TGGGAAAGAG GGACCAGAAC | 1920 |
| TTCCCCTCCC TTCCCCTTTT CCCAACCTGG ACTTGTTTTA | 1960 |
| AACTTGCCTG TTCAGAGCAC TCATTCCTTC CCACCCCCAG | 2000 |
| TCCTGTCCTA TCACTCTAAT TCGGATTTGC CATAGCCTTG | 2040 |
| AGGTAATGTC CTTTTCCATT AAGTACATGT GCCAGGAAAC | 2080 |
| AGCGAGAGAG AGAAAGTAAA CGGCAGTAAT GCTTCTCCTA | 2120 |
| TTTCTCCAAA GCCTTGTGTG AACTAGCAAA GAGAAGAAAA | 2160 |
| TCAAATATAT AACCAATAGT GAAATGCCAC AGGTTTGTCC | 2200 |
| ACTGTCAGGG TTGTCTACCT GTAGGATCAG GGTCTAAGCA | 2240 |
| CCTTGGTGCT TAGCTAGAAT ACCACCTAAT CCTTCTGGCA | 2280 |
| AGCCTGTCTT CAGAGAACCC ACTAGAAGCA ACTAGGAAAA | 2320 |
| ATCACTTGCC AAAATCCAAG GCAATTCCTG ATGGAAAATG | 2360 |
| CAAAAGCACA TATATGTTTT AATATCTTTA TGGGCTCTGT | 2400 |
| TCAAGGCAGT GCTGAGAGGG AGGGGTTATA GCTTCAGGAG | 2440 |
| GGAACCAGCT TCTGATAAAC ACAATCTGCT AGGAACTTGG | 2480 |
| GAAAGGAAT CAGAGAGCTGC CCTTCAGCGA TTATTTAAAT | 2520 |
| TGTTAAAGAA TACACAATTT GGGGTATTGG GATTTTCTC | 2560 |
| CTTTTCTCTG AGACATTCCA CCATTTTAAT TTTTGTAACT | 2600 |
| GCTTATTTAT GTGAAAAGGG TTATTTTTAC TTAGCTTAGC | 2640 |

```
TATGTCAGCC AATCCGATTG CCTTAGGTGA AAGAAACCAC                    2680

CGAAATCCCT CAGGTCCCTT GGTCAGGAGC CTCTCAAGAT                    2720

TTTTTTTGTC AGAGGCTCCA AATAGAAAAT AAGAAAAGGT                    2760

TTTCTTCATT CATGGCTAGA GCTAGATTTA ACTCAGTTTC                    2800

TAGGCACCTC AGACCAATCA TCAACTACCA TTCTATTCCA                    2840

TGTTTGCACC TGTGCATTTT CTGTTTGCCC CCATTCACTT                    2880

TGTCAGGAAA CCTTGGCCTC TGCTAAGGTG TATTTGGTCC                    2920

TTGAGAAGTG GGAGCACCCT ACAGGGACAC TATCACTCAT                    2960

GCTGGTGGCA TTGTTTACAG CTAGAAAGCT GCACTGGTGC                    3000

TAATGCCCCT TGGGAAATGG GGCTGTGAGG AGGAGGATTA                    3040

TAACTTAGGC CTAGCCTCTT TTAACAGCCT CTGAAATTTA                    3080

TCTTTTCTTC TATGGGGTCT ATAAATGTAT CTTATAATAA                    3120

AAAGGAAGGA CAGGAGGAAG ACAGGCAAAT GTACTTCTCA                    3160

CCCAGTCTTC TACACAGATG GAATCTCTTT GGGGCTAAGA                    3200

GAAAGGTTTT ATTCTATATT GCTTACCTGA TCTCATGTTA                    3240

GGCCTAAGAG GCTTTCTCCA GGAGGATTAG CTTGGAGTTC                    3280

TCTATACTCA GGTACCTCTT TCAGGGTTTT CTAACCCTGA                    3320

CACGGACTGT GCATACTTTC CCTCATCCAT GCTGTGCTGT                    3360

GTTATTTAAT TTTTCCTGGC TAAGATCATG TCTGAATTAT                    3400

GTATGAAAAT TATTCTATGT TTTTATAATA AAAATAATAT                    3440

ATCAGACATC GAAAAAAAAA A                                        3461

(2) INFORMATION FOR SEQ ID NO: 7:

(i) SEQUENCE CHARACTERISTICS:
        (A) LENGTH: 1964 nucleotides
        (B) TYPE:  nucleic acid
        (C) STRANDEDNESS: single
        (D) TOPOLOGY:  linear (xi) SEQUENCE DESCRIPTION: SEQ ID NO: 7:

CCGGGGGACA CGCAGGGCCA ACAGTCACAG CAGCCCTGAC                    40

CAGAGCATTC CTGGAGCTCA AGCTCTCTAC AAAGAGGTGG                    80

ACAGAGAAGA CAGCAGAGAC C ATG GGA CCC CCC TCA GCC                119
                        Met Gly Pro Pro Ser Ala
                                        -30

CCT CCC TGC AGA TTG CAT GTC CCC TGG AAG GAG GTC CTG            158
Pro Pro Cys Arg Leu His Val Pro Trp Lys Glu Val Leu
            -25                 -20

CTC ACA GCC TCA CTT CTA ACC TTC TGG AAC CCA CCC ACC            197
Leu Thr Ala Ser Leu Leu Thr Phe Trp Asn Pro Pro Thr
-15             -10                 -5

ACT GCC AAG CTC ACT ATT GAA TCC ACG CCA TTC AAT GTC            236
Thr Ala Lys Leu Thr Ile Glu Ser Thr Pro Phe Asn Val
1                   5                   10

GCA GAG GGG AAG GAG GTT CTT CTA CTC GCC CAC AAC CTG            275
Ala Glu Gly Lys Glu Val Leu Leu Leu Ala His Asn Leu
            15                  20
```

| | | |
|---|---|---|
| CCC CAG AAT CGT ATT GGT TAC AGC TGG TAC AAA GGC GAA<br>Pro Gln Asn Arg Ile Gly Tyr Ser Trp Tyr Lys Gly Glu<br>25                             30                            35 | | 314 |
| AGA GTG GAT GGC AAC AGT CTA ATT GTA GGA TAT GTA ATA<br>Arg Val Asp Gly Asn Ser Leu Ile Val Gly Tyr Val Ile<br>         40                             45                          50 | | 353 |
| GGA ACT CAA CAA GCT ACC CCA GGG CCC GCA TAC AGT GGT<br>Gly Thr Gln Gln Ala Thr Pro Gly Pro Ala Tyr Ser Gly<br>                      55                                    60 | | 392 |
| CGA GAG ACA ATA TAC CCC AAT GCA TCC CTG CTG ATC CAG<br>Arg Glu Thr Ile Tyr Pro Asn Ala Ser Leu Leu Ile Gln<br>65                             70                            75 | | 431 |
| AAC GTC ACC CAG AAT GAC ACA GGA TTC TAC ACC CTA CAA<br>Asn Val Thr Gln Asn Asp Thr Gly Phe Tyr Thr Leu Gln<br>         80                             85 | | 470 |
| GTC ATA AAG TCA GAT CTT GTG AAT GAA GAA GCA ACC GGA<br>Val Ile Lys Ser Asp Leu Val Asn Glu Glu Ala Thr Gly<br>90                             95                         100 | | 509 |
| CAG TTC CAT GTA TAC CCG GAG CTG CCC AAG CCC TCC ATC<br>Gln Phe His Val Tyr Pro Glu Leu Pro Lys Pro Ser Ile<br>         105                         110                      115 | | 548 |
| TCC AGC AAC AAC TCC AAC CCC GTG GAG GAC AAG GAT GCT<br>Ser Ser Asn Asn Ser Asn Pro Val Glu Asp Lys Asp Ala<br>                    120                            125 | | 587 |
| GTG GCC TTC ACC TGT GAA CCT GAG GTT CAG AAC ACA ACC<br>Val Ala Phe Thr Cys Glu Pro Glu Val Gln Asn Thr Thr<br>130                            135                        140 | | 626 |
| TAC CTG TGG TGG GTA AAT GGT CAG AGC CTC CCG GTC AGT<br>Tyr Leu Trp Trp Val Asn Gly Gln Ser Leu Pro Val Ser<br>         145                         150 | | 665 |
| CCC AGG CTG CAG CTG TCC AAT GGC AAC AGG ACC CTC ACT<br>Pro Arg Leu Gln Leu Ser Asn Gly Asn Arg Thr Leu Thr<br>155                            160                        165 | | 704 |
| CTA CTC AGC GTC AAA AGG AAC GAT GCA GGA TCG TAT GAA<br>Leu Leu Ser Val Lys Arg Asn Asp Ala Gly Ser Tyr Glu<br>         170                         175                      180 | | 743 |
| TGT GAA ATA CAG AAC CCA GCG AGT GCC AAC CGC AGT GAC<br>Cys Glu Ile Gln Asn Pro Ala Ser Ala Asn Arg Ser Asp<br>                    185                            190 | | 782 |
| CCA GTC ACC CTG AAT GTC CTC TAT GGC CCA GAT GGC CCC<br>Pro Val Thr Leu Asn Val Leu Tyr Gly Pro Asp Gly Pro<br>195                            200                        205 | | 821 |
| ACC ATT TCC CCC TCA AAG GCC AAT TAC CGT CCA GGG GAA<br>Thr Ile Ser Pro Ser Lys Ala Asn Tyr Arg Pro Gly Glu<br>         210                         215 | | 860 |
| AAT CTG AAC CTC TCC TGC CAC GCA GCC TCT AAC CCA CCT<br>Asn Leu Asn Leu Ser Cys His Ala Ala Ser Asn Pro Pro<br>220                            225                        230 | | 899 |
| GCA CAG TAC TCT TGG TTT ATC AAT GGG ACG TTC CAG CAA<br>Ala Gln Tyr Ser Trp Phe Ile Asn Gly Thr Phe Gln Gln<br>         235                         240                      245 | | 938 |
| TCC ACA CAA GAG CTC TTT ATC CCC AAC ATC ACT GTG AAT<br>Ser Thr Gln Glu Leu Phe Ile Pro Asn Ile Thr Val Asn<br>                    250                            255 | | 977 |
| AAT AGC GGA TCC TAT ATG TGC CAA GCC CAT AAC TCA GCC<br>Asn Ser Gly Ser Tyr Met Cys Gln Ala His Asn Ser Ala<br>260                            265                        270 | | 1016 |
| ACT GGC CTC AAT AGG ACC ACA GTC ACG ATG ATC ACA GTC<br>Thr Gly Leu Asn Arg Thr Thr Val Thr Met Ile Thr Val<br>         275                         280 | | 1055 |

-continued

```
TCT GGA AGT GCT CCT GTC CTC TCA GCT GTG GCC ACC GTC         1094
Ser Gly Ser Ala Pro Val Leu Ser Ala Val Ala Thr Val
285                 290                 295

GGC ATC ACG ATT GGA GTG CTG GCC AGG GTG GCT CTG ATA         1133
Gly Ile Thr Ile Gly Val Leu Ala Arg Val Ala Leu Ile
        300                 305                 310

TAGCAGCCCT GGTGTATTTT CGATATTTCA GGAAGACTGG                 1173

CAGATTGGAC CAGACCCTGA ATTCTTCTAG CTCCTCCAAT                 1213

CCCATTTTAT CCCATGGAAC CACTAAAAAC AAGGTCTGCT                 1253

CTGCTCCTGA AGCCCTATAT GCTGGAGATG ACAACTCAA                  1293

TGAAAATTTA AAGGAAAAAC CCTCAGCCCT GAGGTGTGTG                 1333

CCACTCAGAG ACTTCACCTA ACTAGAGACA GGCAAACTGC                 1373

AAACCANNCC TCTTTCGCTT GGCAGGATGA TGGTGTCATT                 1413

AGTATTTCAC AAGAAGTAGC TTCAGAGGGT AACTTAACAG                 1453

AGTATCAGAT CTATCTTGTC AATCCCAACG TTTTACATAA                 1493

AATAAGCGAT CCTTTAGTGC ACCCAGTGAG TGACATTAGC                 1533

AGCATCTTTA ACACAGCCGT GTGTTCAAGT GTACAGTGGT                 1573

CCTTTTCAGA GTTGGNNNTA CTCCAACTGA AATGTTAAGG                 1613

AAGAAGATAG ATCCAATTAA AAAAAATTAA AACCAATTTA                 1653

AAAAAAAAAA AGAACACAGG AGATTCCAGT CTACTTGAGT                 1693

TAGCATAATA CAGAAGTCCC CTCTACTTTA ACTTTTACAA                 1733

AAAAGTAACC TGAACTAATC TGATGTTAAC CAATGTATTT                 1773

ATTTGTCTGG TTCTGTTTCC TTGTTCCAAT TTGACAAAAC                 1813

CCACTGTTCT TGTATTGTAT TGCCCAGGGG GAGCTATCAC                 1853

TGTACTTGTA GAGTGGTGCT GCTTTAAGTT CATAAATCAC                 1893

AAATAAAAGC CAATTAGCTC TATAACTAAA AAAAAAAAA                  1933

AAAAAAAAAA AAAAAAAAA AAAAAAAAA A                            1964
```

(2) INFORMATION FOR SEQ ID NO: 8:

(i) SEQUENCE CHARACTERISTICS:
        (A) LENGTH: 2009 nucleotides
        (B) TYPE: nucleic acid
        (C) STRANDEDNESS: single
        (D) TOPOLOGY: linear (xi) SEQUENCE DESCRIPTION: SEQ ID NO: 8:

```
ACAGCACAGC TGACAGCCGT ACTCAGGAAG CTTCTGGATC                  40

CTAGGCTTAT CTCCACAGAG GAGAACACAC AAGCAGCAGA                  80

GACC ATG GGG CCC CTC TCA GCC CCT CCC TGC ACA                114
     Met Gly Pro Leu Ser Ala Pro Pro Cys Thr
         1               5                  10

CAC CTC ATC ACT TGG AAG GGG GTC CTG CTC ACA GCA TCA         153
His Leu Ile Thr Trp Lys Gly Val Leu Leu Thr Ala Ser
                15                  20

CTT TTA AAC TTC TGG AAT CCG CCC ACA ACT GCC CAA GTC         192
Leu Leu Asn Phe Trp Asn Pro Pro Thr Thr Ala Gln Val
    25                  30                  35
```

| | |
|---|---|
| ACG ATT GAA GCC CAG CCA CCC AAA GTT TCT GAG GGG AAG<br>Thr Ile Glu Ala Gln Pro Pro Lys Val Ser Glu Gly Lys<br>40                             45 | 231 |
| GAT GTT CTT CTA CTT GTC CAC AAT TTG CCC CAG AAT CTT<br>Asp Val Leu Leu Leu Val His Asn Leu Pro Gln Asn Leu<br>50                     55                  60 | 270 |
| GCT GGC TAC ATT TGG TAC AAA GGG CAA ATG ACA TAC GTC<br>Ala Gly Tyr Ile Trp Tyr Lys Gly Gln Met Thr Tyr Val<br>65                    70                    75 | 309 |
| TAC CAT TAC ATT ACA TCA TAT GTA GTA GAC GGT CAA AGA<br>Tyr His Tyr Ile Thr Ser Tyr Val Val Asp Gly Gln Arg<br>               80                  85 | 348 |
| ATT ATA TAT GGG CCT GCA TAC AGT GGA AGA GAA AGA GTA<br>Ile Ile Tyr Gly Pro Ala Tyr Ser Gly Arg Glu Arg Val<br>90                    95               100 | 387 |
| TAT TCC AAT GCA TCC CTG CTG ATC CAG AAT GTC ACG CAG<br>Tyr Ser Asn Ala Ser Leu Leu Ile Gln Asn Val Thr Gln<br>            105                 110 | 426 |
| GAG GAT GCA GGA TCC TAC ACC TTA CAC ATC ATA AAG CGA<br>Glu Asp Ala Gly Ser Tyr Thr Leu His Ile Ile Lys Arg<br>115               120               125 | 465 |
| CGC GAT GGG ACT GGA GGA GTA ACT GGA CAT TTC ACC TTC<br>Arg Asp Gly Thr Gly Gly Val Thr Gly His Phe Thr Phe<br>         130                 135              140 | 504 |
| ACC TTA CAC CTG GAG ACT CCC AAG CCC TCC ATC TCC AGC<br>Thr Leu His Leu Glu Thr Pro Lys Pro Ser Ile Ser Ser<br>                 145                 150 | 543 |
| AGC AAC TTA AAT CCC AGG GAG GCC ATG GAG GCT GTG ATC<br>Ser Asn Leu Asn Pro Arg Glu Ala Met Glu Ala Val Ile<br>155               160               165 | 582 |
| TTA ACC TGT GAT CCT GCG ACT CCA GCC GCA AGC TAC CAG<br>Leu Thr Cys Asp Pro Ala Thr Pro Ala Ala Ser Tyr Gln<br>         170                 175 | 621 |
| TGG TGG ATG AAT GGT CAG AGC CTC CCT ATG ACT CAC AGG<br>Trp Trp Met Asn Gly Gln Ser Leu Pro Met Thr His Arg<br>180               185               190 | 660 |
| TTG CAG CTG TCC AAA ACC AAC AGG ACC CTC TTT ATA TTT<br>Leu Gln Leu Ser Lys Thr Asn Arg Thr Leu Phe Ile Phe<br>         195               200            205 | 699 |
| GGT GTC ACA AAG TAT ATT GCA GGA CCC TAT GAA TGT GAA<br>Gly Val Thr Lys Tyr Ile Ala Gly Pro Tyr Glu Cys Glu<br>            210               215 | 738 |
| ATA CGG AAC CCA GTG AGT GCC AGC CGC AGT GAC CCA GTC<br>Ile Arg Asn Pro Val Ser Ala Ser Arg Ser Asp Pro Val<br>220               225              230 | 777 |
| ACC CTG AAT CTC CTC CCA AAG CTG TCC AAG CCC TAC ATC<br>Thr Leu Asn Leu Leu Pro Lys Leu Ser Lys Pro Tyr Ile<br>         235               240 | 816 |
| ACA ATC AAC AAC TTA AAC CCC AGA GAG AAT AAG GAT GTC<br>Thr Ile Asn Asn Leu Asn Pro Arg Glu Asn Lys Asp Val<br>245               250              255 | 855 |
| TTA ACC TTC ACC TGT GAA CCT AAG AGT GAG AAC TAC ACC<br>Leu Thr Phe Thr Cys Glu Pro Lys Ser Glu Asn Tyr Thr<br>         260               265            270 | 894 |
| TAC ATT TGG TGG CTA AAT GGT CAG AGC CTC CCT GTC AGT<br>Tyr Ile Trp Trp Leu Asn Gly Gln Ser Leu Pro Val Ser<br>            275               280 | 933 |
| CCC AGG GTA AAG CGA CCC ATT GAA AAC AGG ATC CTC ATT<br>Pro Arg Val Lys Arg Pro Ile Glu Asn Arg Ile Leu Ile<br>285               290              295 | 972 |

```
CTA CCC AAT GTC ACG AGA AAT GAA ACA GGA CCT TAT CAA        1011
Leu Pro Asn Val Thr Arg Asn Glu Thr Gly Pro Tyr Gln
        300                 305

TGT GAA ATA CGG GAC CGA TAT GGT GGC ATC CGC AGT GAC        1050
Cys Glu Ile Arg Asp Arg Tyr Gly Gly Ile Arg Ser Asp
310             315                 320

CCA GTC ACC CTG AAT GTC CTC TAT GGT CCA GAC CTC CCC        1089
Pro Val Thr Leu Asn Val Leu Tyr Gly Pro Asp Leu Pro
            325                 330             335

AGC ATT TAC CCT TCA TTC ACC TAT TAC CGT TCA GGA GAA        1128
Ser Ile Tyr Pro Ser Phe Thr Tyr Tyr Arg Ser Gly Glu
                340                 345

AAC CTC TAC TTT TCC TGC TTC GGT GAG TCT AAC CCA CGG        1167
Asn Leu Tyr Phe Ser Cys Phe Gly Glu Ser Asn Pro Arg
        350                 355                 360

GCA CAA TAT TCT TGG ACA ATT AAT GGG AAG TTT CAG CTA        1206
Ala Gln Tyr Ser Trp Thr Ile Asn Gly Lys Phe Gln Leu
            365                 370

TCA GGA CAA AAG CTC TCT ATC CCC CAA ATA ACT ACA AAG        1245
Ser Gly Gln Lys Leu Ser Ile Pro Gln Ile Thr Thr Lys
375             380                 385

CAT AGT GGG CTC TAT GCT TGC TCT GTT CGT AAC TCA GCC        1284
His Ser Gly Leu Tyr Ala Cys Ser Val Arg Asn Ser Ala
        390                 395                 400

ACT GGC AAG GAA AGC TCC AAA TCC ATC ACA GTC AAA GTC        1323
Thr Gly Lys Glu Ser Ser Lys Ser Ile Thr Val Lys Val
                405                 410

TCT GAC TGG ATA TTA CCC TGAATTCTAC TAGTTCCTCC              1361
Ser Asp Trp Ile Leu Pro
    415

AATTCCATTT TCTCCCATGG AATCACGAAG AGCAAGACCC                1401

ACTCTGTTCC AGAAGCCCTA TAATCTGGAG GTGGACAACT                1441

CGATGTAAAT TTCATGGGAA ACCCTTGTA CCTGACATGT                 1481

GAGCCACTCA GAACTCACCA AAATGTTCGA CACCATAACA                1521

ACAGCTACTC AAACTGTAAA CCAGGATAAG AAGTTGATGA                1561

CTTCACACTG TGGACAGTTT TTCAAAGATG TCATAACAAG                1601

ACTCCCCATC ATGACAAGGC TCCACCCTCT ACTGTCTGCT                1641

CATGCCTGCC TCTTTCACTT GGCAGGATAA TGCAGTCATT                1681

AGAATTTCAC ATGTAGTAGC TTCTGAGGGT AACAACAGAG                1721

TGTCAGATAT GTCATCTCAA CCTCAAACTT TTACGTAACA                1761

TCTCAGGGAA ATGTGGCTCT CTCCATCTTG CATACAGGGC                1801

TCCCAATAGA AATGAACACA GAGATATTGC CTGTGTGTTT                1841

GCAGAGAAGA TGGTTTCTAT AAAGAGTAGG AAAGCTGAAA                1881

TTATAGTAGA GTCTCCTTTA AATGCACATT GTGTGGATGG                1921

CTCTCACCAT TTCCTAAGAG ATACAGTGTA AAAACGTGAC                1961

AGTAATACTG ATTCTAGCAG AATAAACATG TACCACATTT                2001

GCAAAAAA                                                   2009
```

(2) INFORMATION FOR SEQ ID NO: 9:

(i) SEQUENCE CHARACTERISTICS:
      (A) LENGTH: 1591 nucleotides
      (B) TYPE: nucleic acid (C) STRANDEDNESS: single
(D) TOPOLOGY: linear (xi) SEQUENCE DESCRIPTION: SEQ ID NO: 9:

| | |
|---|---:|
| GGGTGGATCC TAGGCTCATC TCCATAGGGG AGAACACACA | 40 |

| | | | | | | | | | | |
|---|---|---|---|---|---|---|---|---|---|---:|
| TACAGCAGAG | ACC | ATG | GGA | CCC | CTC | TCA | GCC | CCT | CCC TGC | 80 |
| | | Met | Gly | Pro | Leu | Ser | Ala | Pro | Pro Cys | |
| | | | | | 5 | | | | | |

| | | | | | | | | | | |
|---|---|---|---|---|---|---|---|---|---|---:|
| ACT | CAG | CAC | ATC | ACC | TGG | AAG | GGG | CTC | CTG CTC ACA GCA | 119 |
| Thr | Gln | His | Ile | Thr | Trp | Lys | Gly | Leu | Leu Leu Thr Ala | |
| 10 | | | | | 15 | | | | 20 | |

| | | | | | | | | | | |
|---|---|---|---|---|---|---|---|---|---|---:|
| TCA | CTT | TTA | AAC | TTC | TGG | AAC | CTG | CCC | ACC ACT GCC CAA | 158 |
| Ser | Leu | Leu | Asn | Phe | Trp | Asn | Leu | Pro | Thr Thr Ala Gln | |
| | | 25 | | | | 30 | | | 35 | |

| | | | | | | | | | | |
|---|---|---|---|---|---|---|---|---|---|---:|
| GTA | ATA | ATT | GAA | GCC | CAG | CCA | CCC | AAA | GTT TCT GAG GGG | 197 |
| Val | Ile | Ile | Glu | Ala | Gln | Pro | Pro | Lys | Val Ser Glu Gly | |
| | | | | 40 | | | | 45 | | |

| | | | | | | | | | | |
|---|---|---|---|---|---|---|---|---|---|---:|
| AAG | GAT | GTT | CTT | CTA | CTT | GTC | CAC | AAT | TTG CCC CAG AAT | 236 |
| Lys | Asp | Val | Leu | Leu | Leu | Val | His | Asn | Leu Pro Gln Asn | |
| 50 | | | | | 55 | | | | 60 | |

| | | | | | | | | | | |
|---|---|---|---|---|---|---|---|---|---|---:|
| CTT | ACT | GGC | TAC | ATC | TTG | TAC | AAA | GGG | CAA ATG ACG GAC | 275 |
| Leu | Thr | Gly | Tyr | Ile | Trp | Tyr | Lys | Gly | Gln Met Thr Asp | |
| | | | | 65 | | | | 70 | | |

| | | | | | | | | | | |
|---|---|---|---|---|---|---|---|---|---|---:|
| CTC | TAC | CAT | TAC | ATT | ACA | TCA | TAT | GTA | GTA GAC GGT CAA | 314 |
| Leu | Tyr | His | Tyr | Ile | Thr | Ser | Tyr | Val | Val Asp Gly Gln | |
| 75 | | | | | 80 | | | | 85 | |

| | | | | | | | | | | |
|---|---|---|---|---|---|---|---|---|---|---:|
| ATT | ATA | TAT | GGG | CCT | GCC | TAC | AGT | GGA | CGA GAA ACA GTA | 353 |
| Ile | Ile | Tyr | Gly | Pro | Ala | Tyr | Ser | Gly | Arg Glu Thr Val | |
| | | | 90 | | | | 95 | | 100 | |

| | | | | | | | | | | |
|---|---|---|---|---|---|---|---|---|---|---:|
| TAT | TCC | AAT | GCA | TCC | CTG | CTG | ATC | CAG | AAT GTC ACA CAG | 392 |
| Tyr | Ser | Asn | Ala | Ser | Leu | Leu | Ile | Gln | Asn Val Thr Gln | |
| | | | | 105 | | | | 110 | | |

| | | | | | | | | | | |
|---|---|---|---|---|---|---|---|---|---|---:|
| GAG | GAT | GCA | GGA | TCC | TAC | ACC | TTA | CAC | ATC ATA AAG CGA | 431 |
| Glu | Asp | Ala | Gly | Ser | Tyr | Thr | Leu | His | Ile Ile Lys Arg | |
| | 115 | | | | 120 | | | | 125 | |

| | | | | | | | | | | |
|---|---|---|---|---|---|---|---|---|---|---:|
| GGC | GAT | GGG | ACT | GGA | GGA | GTA | ACT | GGA | TAT TTC ACT GTC | 470 |
| Gly | Asp | Gly | Thr | Gly | Gly | Val | Thr | Gly | Tyr Phe Thr Val | |
| | | 130 | | | | 135 | | | | |

| | | | | | | | | | | |
|---|---|---|---|---|---|---|---|---|---|---:|
| ACC | TTA | TAC | TCG | GAG | ACT | CCC | AAG | CGC | TCC ATC TCC AGC | 509 |
| Thr | Leu | Tyr | Ser | Glu | Thr | Pro | Lys | Arg | Ser Ile Ser Ser | |
| 140 | | | | | 145 | | | | 150 | |

| | | | | | | | | | | |
|---|---|---|---|---|---|---|---|---|---|---:|
| AGC | AAC | TTA | AAC | CCC | AGG | GAG | GTC | ATG | GAG GCT GTG CGC | 548 |
| Ser | Asn | Leu | Asn | Pro | Arg | Glu | Val | Met | Glu Ala Val Arg | |
| | | 155 | | | | 160 | | | 165 | |

| | | | | | | | | | | |
|---|---|---|---|---|---|---|---|---|---|---:|
| TTA | ATC | TGT | GAT | CCT | GAG | ACT | CCG | GAT | GCA AGC TAC CTG | 587 |
| Leu | Ile | Cys | Asp | Pro | Glu | Thr | Pro | Asp | Ala Ser Tyr Leu | |
| | | | 170 | | | | 175 | | | |

| | | | | | | | | | | |
|---|---|---|---|---|---|---|---|---|---|---:|
| TGG | TTG | CTG | AAT | GGT | CAG | AAC | CTC | CCT | ATG ACT CAC AGG | 626 |
| Trp | Leu | Leu | Asn | Gly | Gln | Asn | Leu | Pro | Met Thr His Arg | |
| | 180 | | | | 185 | | | | 190 | |

| | | | | | | | | | | |
|---|---|---|---|---|---|---|---|---|---|---:|
| TTG | CAG | CTG | TCC | AAA | ACC | AAC | AGG | ACC | CTC TAT CTA TTT | 665 |
| Leu | Gln | Leu | Ser | Lys | Thr | Asn | Arg | Thr | Leu Tyr Leu Phe | |
| | | | 195 | | | | 200 | | | |

| | | | | | | | | | | |
|---|---|---|---|---|---|---|---|---|---|---:|
| GGT | GTC | ACA | AAG | TAT | ATT | GCA | GGG | CCC | TAT GAA TGT GAA | 704 |
| Gly | Val | Thr | Lys | Tyr | Ile | Ala | Gly | Pro | Tyr Glu Cys Glu | |
| 205 | | | | | 210 | | | | 215 | |

| | | | | | | | | | | |
|---|---|---|---|---|---|---|---|---|---|---:|
| ATA | CGG | AGG | GGA | GTG | AGT | GCC | AGC | CGC | AGT GAC CCA GTC | 743 |
| Ile | Arg | Arg | Gly | Val | Ser | Ala | Ser | Arg | Ser Asp Pro Val | |
| | | 220 | | | | 225 | | | 230 | |

| | |
|---|---|
| ACC CTG AAT CTC CTC CCG AAG CTG CCC ATG CCT TAC ATC<br>Thr Leu Asn Leu Leu Pro Lys Leu Pro Met Pro Tyr Ile<br>235                          240 | 782 |
| ACC ATC AAC AAC TTA AAC CCC AGG GAG AAG AAG GAT GTG<br>Thr Ile Asn Asn Leu Asn Pro Arg Glu Lys Lys Asp Val<br>245                   250                   255 | 821 |
| TTA GCC TTC ACC TGT GAA CCT AAG AGT CGG AAC TAC ACC<br>Leu Ala Phe Thr Cys Glu Pro Lys Ser Arg Asn Tyr Thr<br>           260                   265 | 860 |
| TAC ATT TGG TGG CTA AAT GGT CAG AGC CTC CCG GTC AGT<br>Tyr Ile Trp Trp Leu Asn Gly Gln Ser Leu Pro Val Ser<br>270                   275                   280 | 899 |
| CCG AGG GTA AAG CGA CCC ATT GAA AAC AGG ATA CTC ATT<br>Pro Arg Val Lys Arg Pro Ile Glu Asn Arg Ile Leu Ile<br>           285                   290                  295 | 938 |
| CTA CCC AGT GTC ACG AGA AAT GAA ACA GGA CCC TAT CAA<br>Leu Pro Ser Val Thr Arg Asn Glu Thr Gly Pro Tyr Gln<br>                300                   305 | 977 |
| TGT GAA ATA CGG GAC CGA TAT GGT GGC ATC CGC AGT AAC<br>Cys Glu Ile Arg Asp Arg Tyr Gly Gly Ile Arg Ser Asn<br>310                   315                   320 | 1016 |
| CCA GTC ACC CTG AAT GTC CTC TAT GGT CCA GAC CTC CCC<br>Pro Val Thr Leu Asn Val Leu Tyr Gly Pro Asp Leu Pro<br>           325                         330 | 1055 |
| AGA ATT TAC CCT TAC TTC ACC TAT TAC CGT TCA GGA GAA<br>Arg Ile Tyr Pro Tyr Phe Thr Tyr Tyr Arg Ser Gly Glu<br>335                   340                   345 | 1094 |
| AAC CTC GAC TTG TCC TGC TTT GCG GAC TCT AAC CCA CCG<br>Asn Leu Asp Leu Ser Cys Phe Ala Asp Ser Asn Pro Pro<br>           350                   355                   360 | 1133 |
| GCA GAG TAT TTT TGG ACA ATT AAT GGG AAG TTT CAG CTA<br>Ala Glu Tyr Phe Trp Thr Ile Asn Gly Lys Phe Gln Leu<br>                365                   370 | 1172 |
| TCA GGA CAA AAG CTC TTT ATC CCC CAA ATT ACT ACA AAT<br>Ser Gly Gln Lys Leu Phe Ile Pro Gln Ile Thr Thr Asn<br>375                   380                   385 | 1211 |
| CAT AGC GGG CTC TAT GCT TGC TCT GTT CGT AAC TCA GCC<br>His Ser Gly Leu Tyr Ala Cys Ser Val Arg Asn Ser Ala<br>           390                   395 | 1250 |
| ACT GGC AAG GAA ATC TCC AAA TCC ATG ATA GTC AAA GTC<br>Thr Gly Lys Glu Ile Ser Lys Ser Met Ile Val Lys Val<br>400                   405                   410 | 1289 |
| TCT GGT CCC TGC CAT GGA AAC CAG ACA GAG TCT CAT<br>Ser Gly Pro Cys His Gly Asn Gln Thr Glu Ser His<br>           415                   420 | 1325 |
| TAATGGCTGC CACAATAGAG ACACTGAGAA AAAGAACAGG | 1365 |
| TTGATACCTT CATGAAATTC AAGACAAAGA AGAAAAAGGC | 1405 |
| TCAATGTTAT TGGACTAAAT AATCAAAAGG ATAATGTTTT | 1445 |
| CATAATTTTT ATTGGAAAAT GTGCTGATTC TTGGAATGTT | 1485 |
| TTATTCTCCA GATTTATGAA CTTTTTTTCT TCAGCAATTG | 1525 |
| GTAAAGTATA CTTTTGTAAA CAAAAATTGA AACATTTGCT | 1565 |
| TTTGCTCTCT ATCTGAGTGC CCCCCC | 1591 |

(2) INFORMATION FOR SEQ ID NO: 10:

(i) SEQUENCE CHARACTERISTICS:
       (A) LENGTH: 12 nucleotides
       (B) TYPE:  nucleic acid

```
            (C) STRANDEDNESS: single
            (D) TOPOLOGY:    linear (xi) SEQUENCE DESCRIPTION:  SEQ ID NO: 10:

GCTCCTTGTA AG                                                           12

(2) INFORMATION FOR SEQ ID NO: 11:

(i) SEQUENCE CHARACTERISTICS:
            (A) LENGTH: 12 nucleotides
            (B) TYPE:   nucleic acid
            (C) STRANDEDNESS: single
            (D) TOPOLOGY:    linear (xi) SEQUENCE DESCRIPTION:  SEQ ID NO: 11:

GCT GGT TGT AAG                                                         12
Ala Gly Cys Lys (2) INFORMATION FOR SEQ ID NO: 12:

(i) SEQUENCE CHARACTERISTICS:
            (A) LENGTH: 12 nucleotides
            (B) TYPE:   nucleic acid
            (C) STRANDEDNESS: single
            (D) TOPOLOGY:    linear (xi) SEQUENCE DESCRIPTION:  SEQ ID NO: 12:

G CTG GTT GTA AG                                                        12
  Leu Val Val (2) INFORMATION FOR SEQ ID NO: 13:

(i) SEQUENCE CHARACTERISTICS:
            (A) LENGTH: 12 nucleotides
            (B) TYPE:   nucleic acid
            (C) STRANDEDNESS: single
            (D) TOPOLOGY:    linear (xi) SEQUENCE DESCRIPTION:  SEQ ID NO: 13:

GC TGG TTG TAAG                                                         12
   Trp Leu (2) INFORMATION FOR SEQ ID NO: 14:

(i) SEQUENCE CHARACTERISTICS:
            (A) LENGTH: 10 nucleotides
            (B) TYPE:   nucleic acid
            (C) STRANDEDNESS: single
            (D) TOPOLOGY:    linear (xi) SEQUENCE DESCRIPTION:  SEQ ID NO: 14:

GGGCCCTTAA                                                              10
```